(12) United States Patent
Heath

(10) Patent No.: US 8,078,288 B2
(45) Date of Patent: Dec. 13, 2011

(54) ELECTRODE SYSTEM FOR A PHYSIOLOGICAL STIMULATOR

(76) Inventor: Roger Lee Heath, Tempe, AZ (US)

( * ) Notice: Subject to any disclaimer, the term of this patent is extended or adjusted under 35 U.S.C. 154(b) by 779 days.

(21) Appl. No.: 11/332,713

(22) Filed: Jan. 13, 2006

(65) Prior Publication Data

US 2006/0155354 A1    Jul. 13, 2006

Related U.S. Application Data

(60) Provisional application No. 60/644,123, filed on Jan. 13, 2005.

(51) Int. Cl.
*A61N 1/08* (2006.01)
*A61N 1/39* (2006.01)
*A61N 1/37* (2006.01)

(52) U.S. Cl. .......................................... 607/142; 607/5

(58) Field of Classification Search ............... 607/2, 142, 607/4, 5, 7

See application file for complete search history.

(56) References Cited

U.S. PATENT DOCUMENTS

| 5,381,050 | A | * | 1/1995 | Siclari et al. ................... 307/112 |
| 6,212,431 | B1 | | 4/2001 | Hahn et al. |
| 6,289,243 | B1 | * | 9/2001 | Lin et al. ............................ 607/5 |
| 7,220,235 | B2 | * | 5/2007 | Geheb et al. .................... 601/41 |
| 7,277,751 | B2 | | 10/2007 | Dupelle et al. |
| 2002/0158775 | A1 | | 10/2002 | Wallace |
| 2003/0171798 | A1 | | 9/2003 | Nova et al. |

* cited by examiner

*Primary Examiner* — Carl H. Layno
*Assistant Examiner* — Tammie K Heller
(74) *Attorney, Agent, or Firm* — Adam K Sacharoff; Much Shelist

(57) ABSTRACT

A physiological power source is coupled to a signal coupler/decoupler through a conductive line. The signal coupler/decoupler includes a proximal signal port, connected to the physiological power source through the first conductive line, and separate distal signal ports. The signal coupler/decoupler combines signals flowing to the physiological power source through the distal signal ports and separates a signal flowing away from it through the proximal signal port.

6 Claims, 14 Drawing Sheets

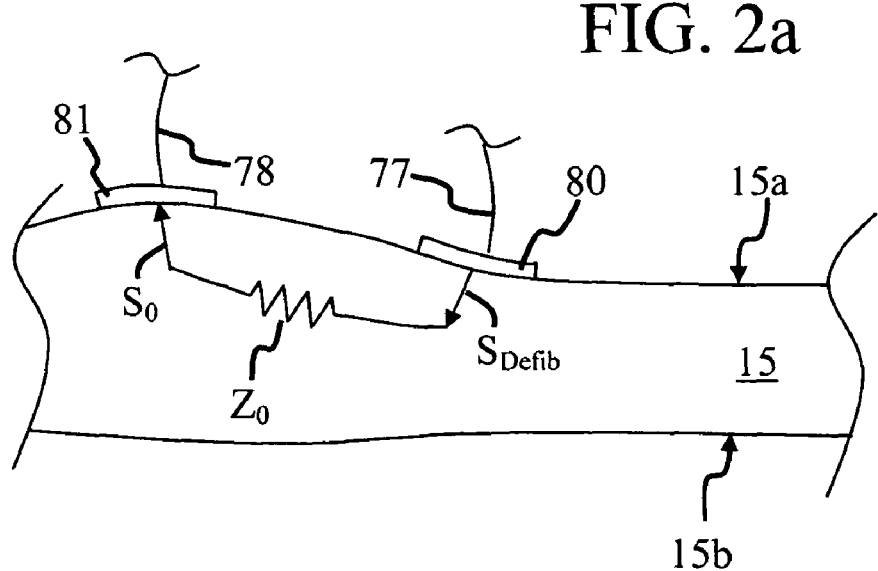
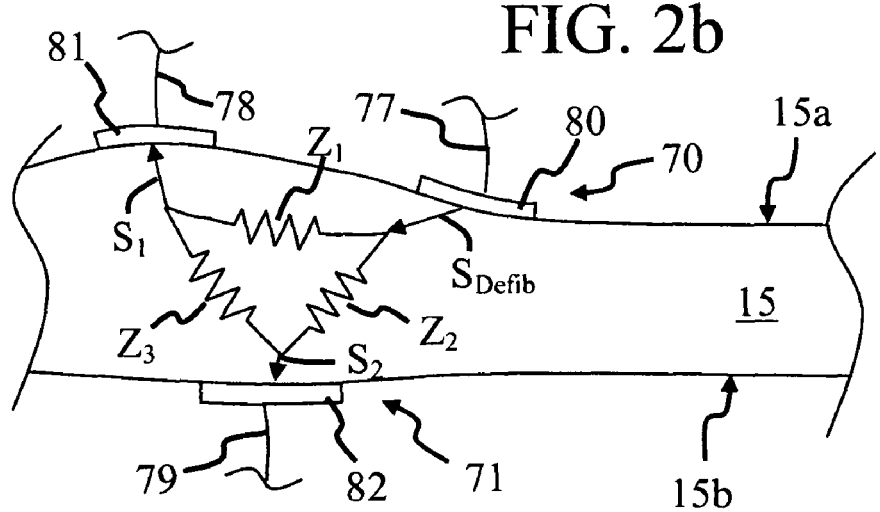
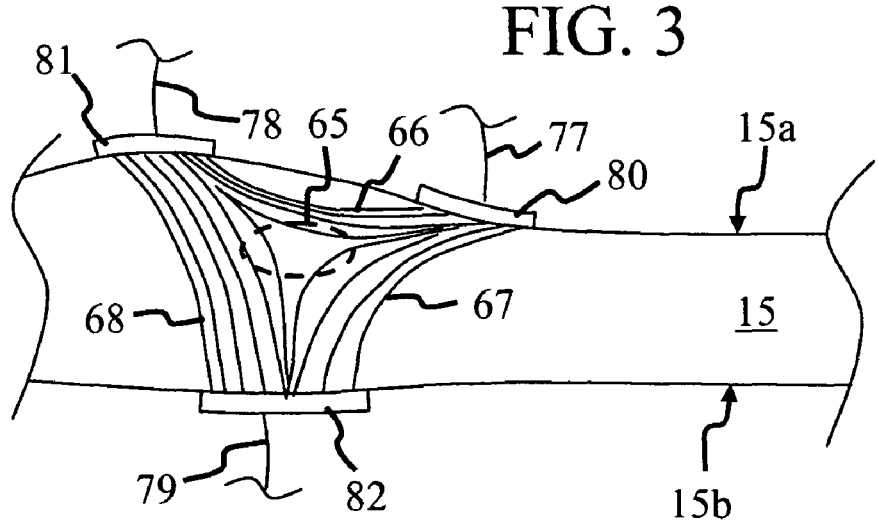

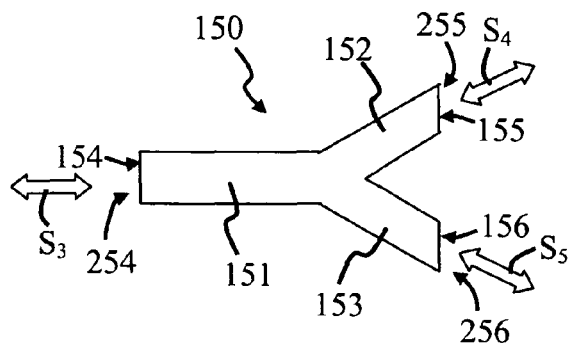
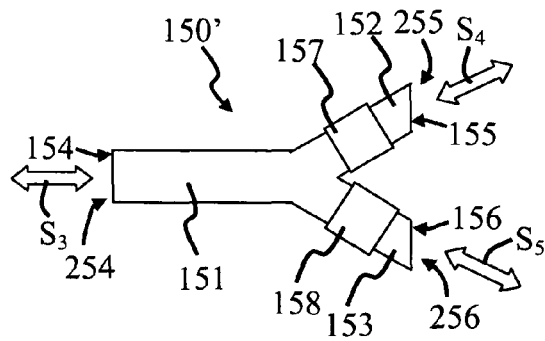
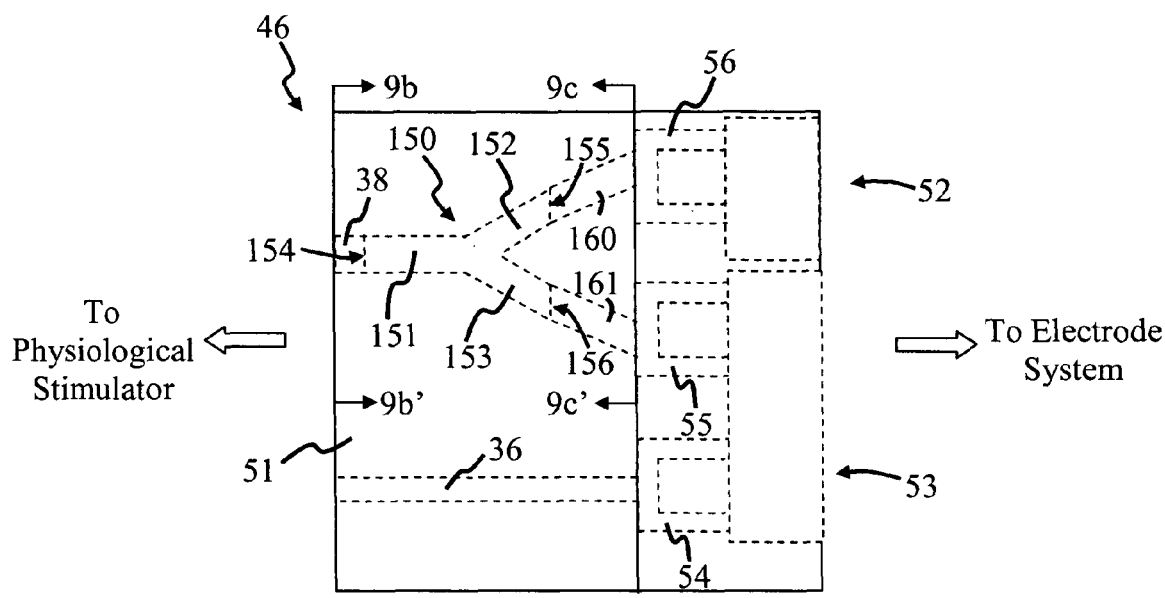
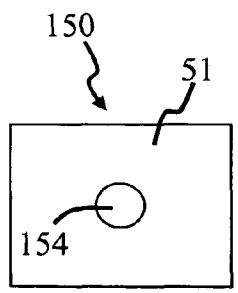
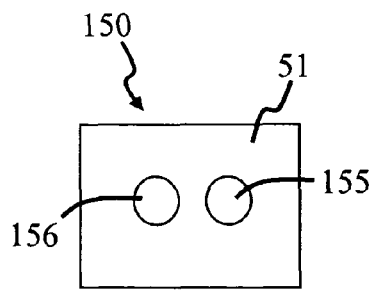

Impedance $Z_{Total}$

ELECTRODE SYSTEM FOR A PHYSIOLOGICAL STIMULATOR

CROSS-REFERENCE TO RELATED APPLICATIONS

This application claims the benefit of U.S. Provisional Application Ser. No. 60/644,123, filed on Jan. 13, 2005.

BACKGROUND OF THE INVENTION

1. Field of the Invention

This invention relates generally to surgery and, more particularly, to electrode systems for use with physiological stimulators.

2. Description of the Related Art

A number of people suffer from arrhythmias each year, such as ventricular fibrillation (VF) and atrial fibrillation (AF), and are often referred to as cardiac patients. It is known that the chances of survival increase if the time between the onset of the arrhythmia and medical treatment is decreased. For example, a cardiac patient's chances of survival decrease about 10% for every minute that elapses after VF begins and before medical treatment, such as defibrillation, is initiated. Since most cardiac patients are away from a hospital at the onset of VF, physiological stimulators, such as automatic external defibrillators (AEDs), pacers, and other medical equipment, have been developed which can be brought to the patient.

An AED defibrillates a patient's heart by providing a defibrillation signal through an electrode system coupled between the patient and AED. The patient's heart is defibrillated in response to the defibrillation signal. The electrode system generally includes an electrode set having a conductive line extending between a connector at one end and an electrode pad at its other end. The electrode set generally includes two conductive lines connected to separate electrode pads and the same connector. The connector and electrode pads couple the conductive lines to the AED and patient, respectively, so that the defibrillation signal flows between them through the conductive lines. Most electrode pads of these types are self-adhesive and disposable.

There are two well accepted placements for these electrode pads. In a first instance, the two electrode pads are placed on the anterior or front portion of the patient's chest in an anterior-anterior placement. In the first instance, one of the pads is placed near the lower left of the patient's thorax near the heart's apex (anterior-apex position) and the other one is positioned on the upper right thorax to the right of the patient's sternum (anterior-sternum position). In a second instance, a first electrode pad is positioned at the anterior-apex position and the second electrode pad is positioned on the posterior or back of the patient (posterior position). In the second instance, the positioning of the electrode pads is typically called an anterior-posterior placement.

There are several problems not addressed by current AEDs and their electrode systems. One problem is that a first responder to a cardiac patient is generally a layperson who provides Basic Life Support (BLS), which includes defibrillation. The first responder preferably uses the anterior-anterior placement for the electrode pads since it is simpler and the first responder is typically not very medically trained. However, when emergency paramedics arrive as second responders, they may prefer to use the anterior-posterior placement because defibrillation and pacing are more effective.

As a result, the electrode system of the first responder is often removed and replaced with that of the second responder in the anterior-posterior placement. If the electrode system of the first responder is not removed, then that of the second responder can be coupled to the patient next to the electrode system of the first responder. This is not desired since the placement of the electrode pads significantly affects the effectiveness of the defibrillation and/or pacing and the health of the patient can be negatively impacted if the correct position is not used.

Further, emergency paramedics generally apply Advanced Life Support (ALS) protocols as recommended by the American Heart Association (AHA). ALS procedures typically include providing various combinations of external pacing, defibrillation, and/or monitoring. Hence, when more advanced medical equipment arrives at the scene, a greater number of different connectors and electrode pads are introduced into the situation.

One type of electrode pads is called QUIK COMBO pads provided by Medtronic, Inc. These electrode pads are useful for monitoring, defibrillation, and pacing. However, when demand pacing is implemented, the monitoring signal is corrupted and separate monitoring electrode pads must be applied to the patient. The monitoring electrode pads are used for electrocardiogram (ECG) monitoring. This is because the QUIK COMBO electrode pads are not effective for monitoring when the patient is being demand paced.

These problems are compounded because some defibrillator manufacturers have designed their electrode systems so that they have connectors that are compatible only with their type of medical equipment and are not compatible with the medical equipment made by other manufacturers. Because of this, if the electrode system of the first responder is not compatible with the AED of the second responder, it is removed from the patient and replaced with an electrode system of the second responder that is compatible.

This is undesirable for several reasons, with one being that it wastes time. Another reason is that more electrode systems are used and the costs increase because they are typically used once and discarded. Multiple pad changes can also cause the skin of the patient to become irritated. Further, in certain situations, it is undesirable to remove a first set of electrode pads already coupled to the patient.

For example, when the patient's heart is being paced in response to a pacing signal flowing through the first set of electrode pads, it is sometimes undesirable to stop pacing. The pacing will be stopped if the first set of electrode pads is removed. In one situation, they are removed so that they can be replaced with a second set of electrode pads. The pacing can be restarted using the second set of electrode pads after they are coupled to the patient, but if it is not done in time, then the health of the patient can be negatively impacted so that his or her chances of survival decrease. Restarting the pacing is sometimes referred to in the art as pacing recapture.

As a result, the incompatibilities in electrode systems made by different manufacturers and the resulting delays in removing and replacing them undesirably interferes with the medical treatment of the patient. Accordingly, what is needed is an electrode system that is compatible with the medical equipment of the different manufacturers. What is also needed is an electrode system that can be changed between different configurations and placements without negatively impacting the health of the patient. There is also a need for a method of providing non-invasive demand pacing that reduces costs, the number of pads used, and the time needed to apply the electrode pads. Further, there is a need for an efficacious method which eliminates corruption of the ECG heart monitoring signal during demand pacing.

BRIEF SUMMARY OF THE INVENTION

The present invention provides an electrode system which includes a connector that allows an electrode set included therein to be used with external non-invasive physiological stimulators made by different manufacturers. For example, an electrode set made by one manufacturer can be used with the physiological stimulator of another manufacturer. The connector also allows the configuration of the electrode system to be changed without negatively impacting the health of the patient. The configuration of the electrode system is changed when the number of electrode pads included therein changes. For example, when the patient is being paced, the number of electrode pads included in the electrode system can be changed without stopping the pacing. As mentioned, the patient's health can be negatively impacted if he or she is being paced and the pacing is stopped.

The invention also provides a signal coupler/decoupler in communication with a physiological power source included in the physiological stimulator. The coupler/decoupler combines signals flowing to the physiological power source and separates a signal flowing away from it. The coupler/decoupler is used to couple two electrode pads together so that the potential difference between them is driven to zero and the two electrode pads operate together as a single electrode pad. The two electrode pads can be engaged and disengaged to the coupler/decoupler independently of each other so that the configuration of the electrode system can be changed.

The invention further provides an impedance sensing circuit that determines the impedance of a patient through the electrode system coupled between the patient and physiological stimulator. The impedance depends on the number of electrode pads included in the electrode system and corresponds to the patient's transthoracic impedance and the contact impedance between the electrode system and patient. Accordingly, the number of electrode pads included in the electrode system can be determined using the impedance sensing circuit.

These and other features, aspects, and advantages of the present invention will become better understood with reference to the following drawings, description, and claims.

BRIEF DESCRIPTION OF THE DRAWINGS

FIGS. 2a and 2b are partial side views of the patient of FIGS. 1a and 1b showing the impedance and signal flow through the patient;

FIG. 3 is a side view of the patient of FIGS. 1a and 1b showing bioelectric field lines which extend through the patient in response to a signal provided by the physiological stimulator through the electrode system;

FIGS. 8a and 8b are top views of different embodiments of the coupler/decoupler of FIGS. 6a and 6b, in accordance with the present invention;

FIG. 9a is a top view of a connector, in accordance with the present invention, which houses the coupler/decoupler of FIG. 8a;

FIG. 9b is a side view of the coupled end of the coupler/decoupler shown in FIG. 9a;

FIG. 9c is a side view of the decoupled ends of the coupler/decoupler shown in FIG. 9a;

FIG. 16a is a view of another embodiment of the connector of FIG. 15c taken along cut line 15c-15c' of FIG. 6a;

FIG. 16b is a view of another connector of FIG. 6a that is compatible with the connector of FIG. 16a.

DETAILED DESCRIPTION OF THE INVENTION

The invention employs an electrode system which includes a connector that allows an electrode set included therein to be used with external non-invasive physiological stimulators provided by different manufacturers. For example, the connector allows an electrode set made by one manufacturer to be used with the AED of another manufacturer so that the connector operates as an adapter. The connector also allows the number of electrode pads included in the electrode system to be changed so that its configuration can be changed. For example, if two electrode pads are being used in a first electrode set, then the configuration is changed by adding a second electrode set to the electrode system. In one example, the second electrode set includes a third electrode pad. This can be done without removing and replacing the electrode pads in the first electrode set already coupled to a patient.

For example, if an anterior-anterior placement of the electrode pads is being used in the first electrode set, then the connector allows a posterior electrode pad to be added to the electrode system as the third electrode. This is preferably done without removing the electrode pads in the first electrode set from the patient. In another example, if an anterior-posterior placement of the electrode pads is being used in the first electrode set, then the connector allows another anterior electrode pad to be added as the third electrode. This is preferably done without removing the electrode pads in the first electrode set. In both of these examples, the two anterior electrode pads, as well as the posterior one, can be used to defibrillate, pace, and/or monitor the patient, as will be discussed below.

Figure 1A:
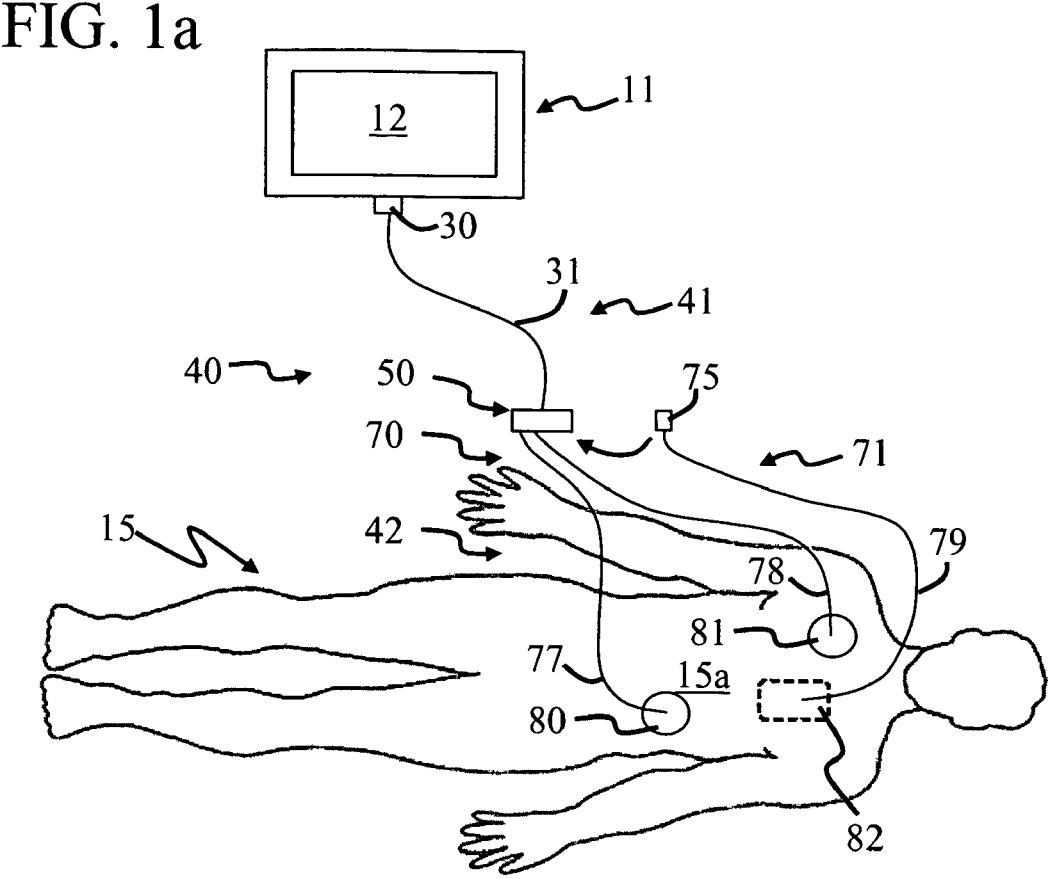
FIGS. 1a and 1b are top views of a physiological stimulator coupled to a patient through an electrode system, in accordance with the present invention.
Figure 1B:
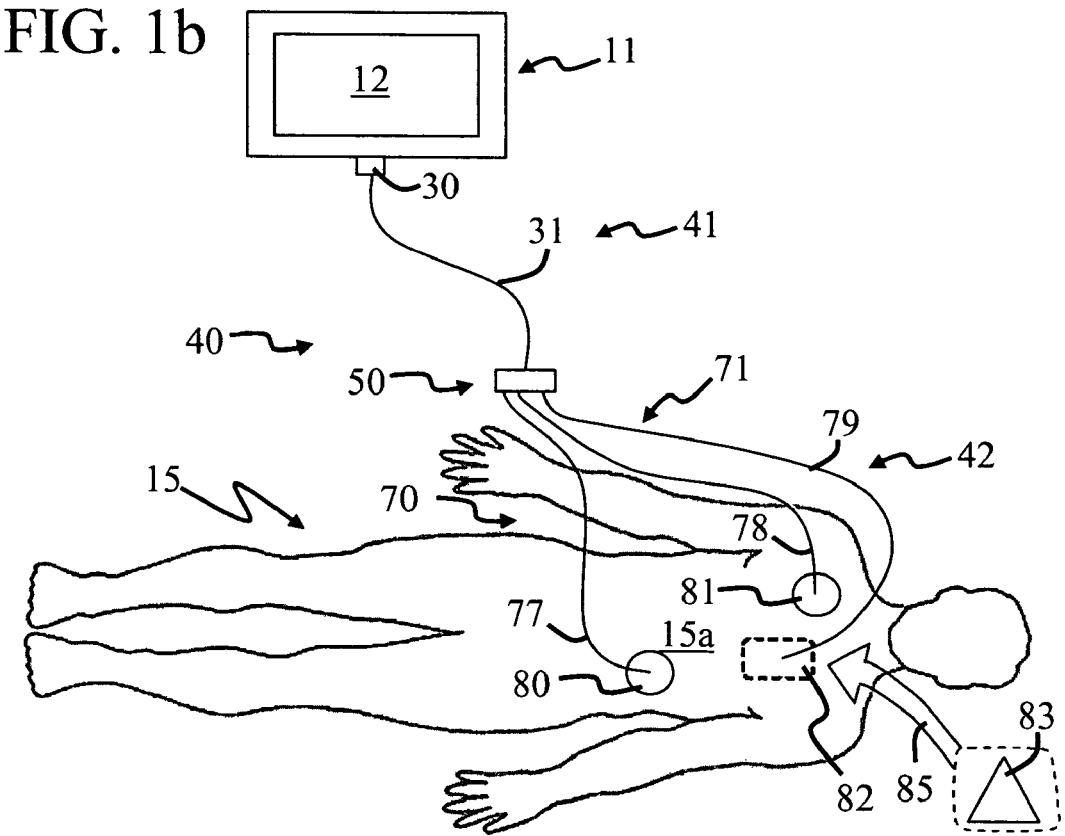

FIGS. 1a and 1b are top views of a physiological stimulator 11 coupled to a patient 15 through an electrode system 40. In this embodiment, electrode system 40 includes an equipment side portion 41 and patient side portion 42. Equipment side portion 41 includes a physiological stimulator cable 31 with a physiological stimulator connector 30 carried at one end and a physiological stimulator connector 50 carried at its other end. Electrode system 40 is connected to a physiological power source 12 included in physiological stimulator 11 through connector 30 and to patient side portion 42 through connector 50. Stimulator 11 operates as an AED in this example, but it can operate as a pacer and/or monitor in other examples and can provide various combinations of defibrillating, pacing, and monitoring functions, as will be discussed in more detail below.

Physiological stimulator 11 can be of many different types which are made by many different manufacturers. For example, Medtronic makes the LIFEPAK CR PLUS and the LIFEPAK 500 AEDs, which are compatible with QUIK COMBO electrode pads. More information about these electrode pads or similar ones can be found in U.S. Pat. Nos. 5,824,033, 5,733,324, 5,571,165, and, which are incorporated herein by reference.

Zoll Medical Corporation makes the Zoll AED which is compatible with STATZ PADS. These electrode pads or similar ones are disclosed in U.S. Pat. No. 6,280,463, which is incorporated herein by reference. Philips Medical Systems makes HEARTSTART electrode pads which are compatible with the HEARTSTART and HEARTSTART MRX AEDs. R2 electrode pads are disclosed in U.S. Pat. Nos. 4,895,169, 4,852,585, 4,850,356, 4,834,103, 4,653,503, 4,494,552, and 4,419,998 by the inventor of the present inventions, the entirety of which are incorporated herein by reference.

More information about defibrillators and electrode pads can be found in U.S. Pat. Nos. 6,694,187, 6,668,192, 6,047,212, 5,782,878, 5,725,560, and 4,102,332, which are incorporated herein by reference. U.S. patent application Ser. No. 11/235,005 filed on Sep. 26, 2005 by the same inventor also provides more understanding of the present invention and is incorporated herein by reference. The present invention can also be used with the physiological stimulator electrode pads and medical system discussed in a copending patent application Ser. No. 11/331,737, entitled "Medical Resuscitation System and Patient Information Module", filed on the same day as the present invention by the same inventor, and incorporated herein by reference. It should be further noted that there are physiological stimulators and their corresponding electrode systems made by other manufacturers, but they are not discussed here for simplicity.

In FIG. 1a, patient side portion 42 includes an electrode set 70 with conductive lines 77 and 78, which are connected to electrode pads 80 and 81, respectively, at one end and connector 50 at their other end. Conductive lines 77 and 78 are in communication with cable 31 through connector 50 and electrode pads 80 and 81 are coupled to anterior 15a of patient 15 in the anterior-anterior placement. Also shown in FIG. 1a is an electrode set 71 with a conductive line 79 connected to a connector 75 at one end and a posterior electrode pad 82 at its other end. Connector 75 is dimensioned and shaped so it can be added to patient side portion 42 by connecting it to connector 50, as shown in FIG. 1b. In this way, it is in communication with cable 31 through connector 50. Posterior electrode pad 82 is positioned on posterior 15b (FIG. 2b) of patient 15 and is shown in phantom in FIGS. 1a and 1b. In other examples, electrode pad 81 is the posterior electrode pad and electrode pad 82 is the anterior-apex electrode pad. Therefore, when an anterior-posterior placement is initially used, anterior-sternum electrode pad 80 is added to electrode system 40 instead of the posterior one.

In accordance with the invention, connector 75 is repeatably moveable between engaged and disengaged positions relative to connector 50 so that electrode set 71 can be added to and removed from electrode system 40 without decoupling electrode pads 80 and 81 from patient 15. Further, this can be done without disconnecting conductive lines 77 and 78 from connector 50. In this way, a signal provided by physiological power source 12 can flow through conductive lines 77 and 78 while electrode set 71 is added to electrode system 40. The signal generally includes a defibrillation signal $S_{Defib}$, pacing signal $S_{Pace}$, and/or monitor signal $S_{Monitor}$, as discussed in more detail below. The dimensions and shapes of the various connectors included herein will be discussed in more detail with FIGS. 15a-15d and 16a-16b below.

It should be noted that electrode pad 82 can have many different shapes. For example, it can be circular like electrode pads 80 and 81 or it can be square, oval, or rectangular. In other examples, it can be triangularly shaped like a posterior electrode pad 83 shown in FIG. 1b. Hence, electrode pad 82 can be replaced by pad 83 as indicated by substation arrow 85. Electrode pad 83, as well as pad 82, preferably has an area that is larger than that of electrode pads 80 and 81. As discussed in more detail below, an electrode pad with a larger conductive skin contact area has a smaller contact impedance than an electrode pad with a smaller conductive contact area. It should be noted that the area of an electrode pad depends on its dimensions, such as its length, width, radius, etc.

In FIG. 1b, pads 81 and 82 can be at the same voltage potential or they can be at different potentials. In one example, pads 81 and 82 have the same potential and operate as a current return for AC and/or DC signals provided by physiological power source 12. If pads 81 and 82 are at the same potential, they preferably cooperate together to operate as a single electrode pad with a larger area and a corresponding smaller impedance than they have individually. This is because the contact impedance between an electrode pad and a patient's skin is inversely proportional to the conductive contact area of the electrode pad. Hence, as its contact area increases, the contact impedance decreases.

Decreasing the contact impedance is advantageous for several reasons. One reason is that it is highly desirable to defibrillate the cardiac patient in the first attempt and the likelihood of this occurring increases as the contact impedance decreases. Further, it is well-known that some patients have higher transthoracic impedances than others. The transthoracic impedance of a patient depends on several factors, such as weight, skin type, etc. Hence, it is desirable to reduce the contact impedance of these patients to increase the likelihood of defibrillating him or her in the first attempt.

Another reason decreasing the contact impedance is advantageous is that as the contact impedance between patient 15 and electrode system 40 decreases, he or she can be defibrillated with a smaller amplitude defibrillation signal. Using a smaller amplitude defibrillation signal provides several advantages. One advantage is that physiological stimulator 11 is safer because it provides lower amplitude signals which are less likely to injure a user of physiological stimulator 11 as well as patient 15. Another advantage is that lower amplitude signals do less damage, such as heart tissue damage and/or skin burning, to patient 15. It can also cause unwanted skeletal muscle contractions, which are painful and difficult to manage.

Further, physiological stimulator 11 can be made less expensive because electronic components that operate with small signal amplitudes tend to be less expensive than those that operate with high signal amplitudes. The overall dimensions of stimulator 11 also decrease because the dimensions of the electronic components included therein are smaller if lower power electronic components are used. For example, low power capacitors are typically smaller than high power capacitors.

Figure 5:
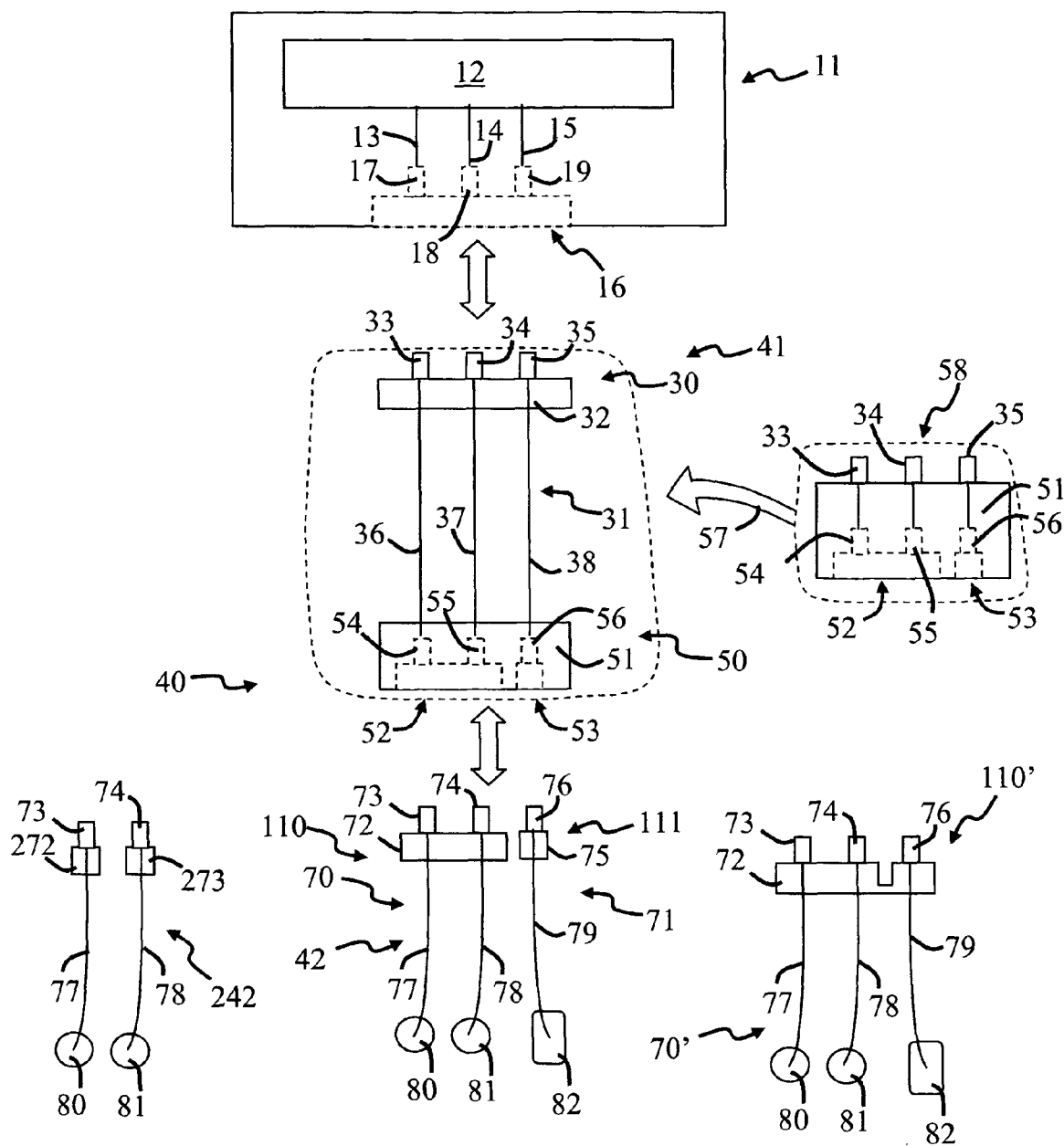
FIG. 5 is a more detailed top view of the electrode system of FIGS. 1a and 1b coupled to the physiological power source, in accordance with the invention.
Figure 6A:
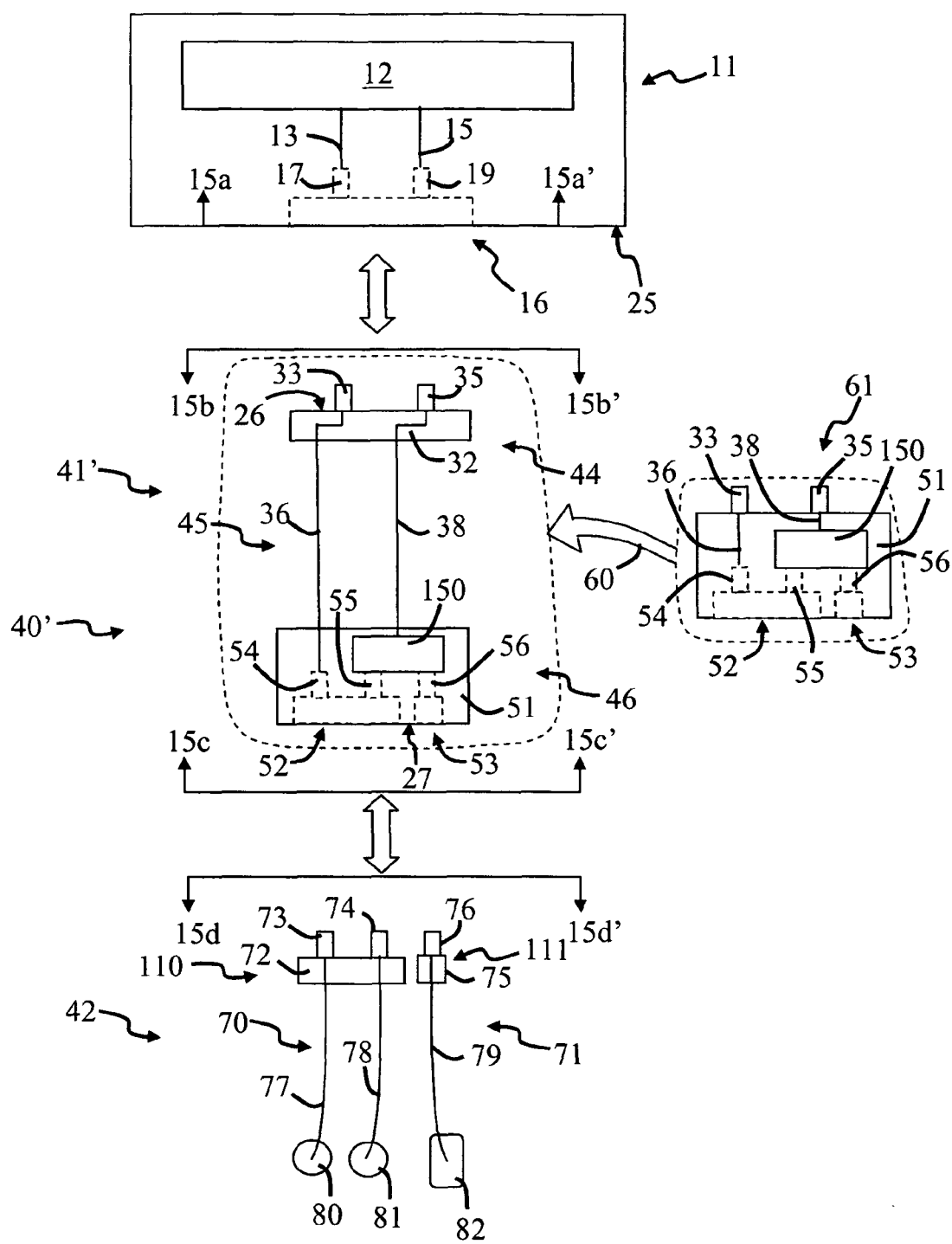
FIG. 6a is a top view of an embodiment of an electrode system with a coupler/decoupler, in accordance with the invention.
Figure 6B:
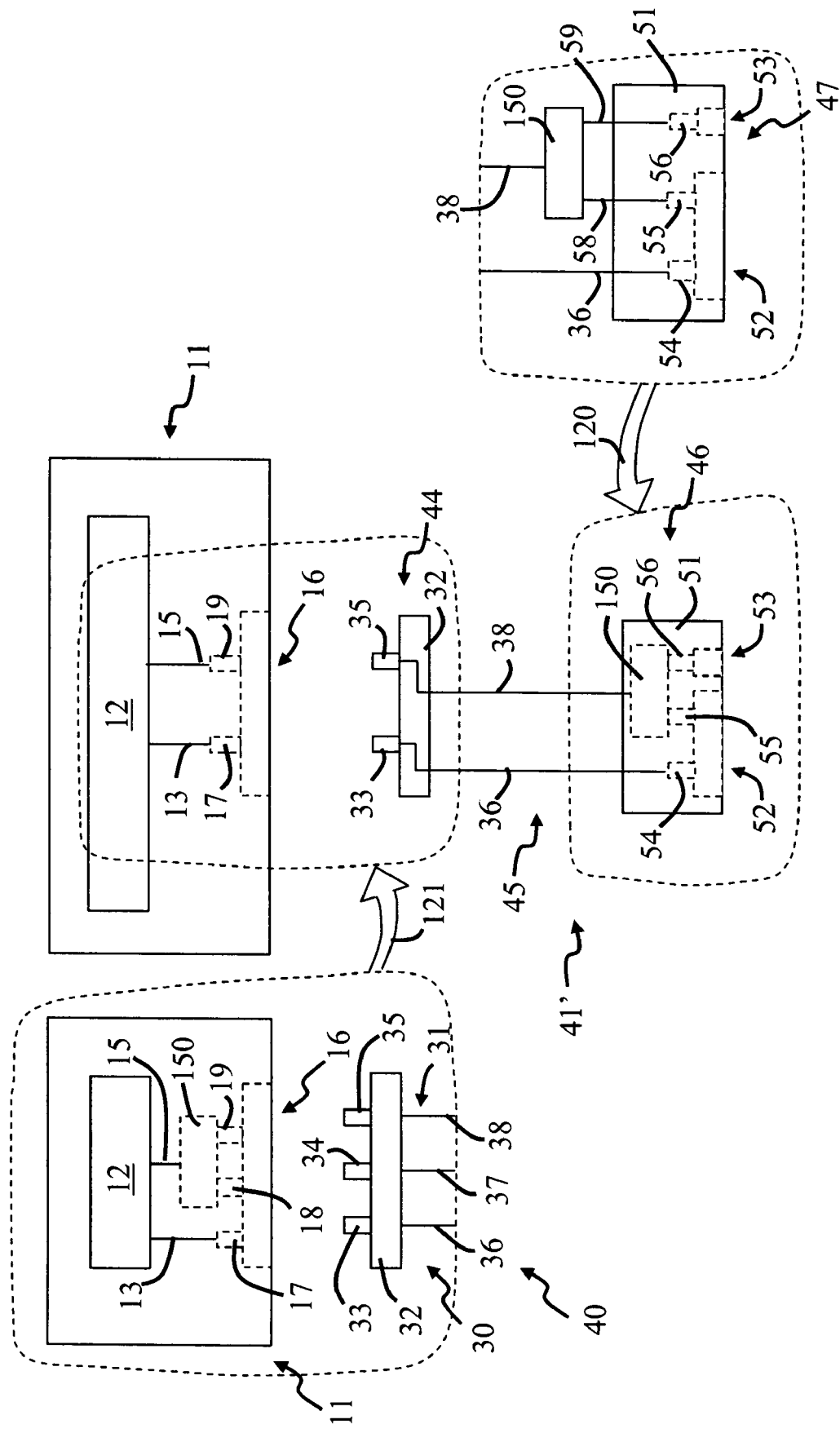
FIG. 6b is a top view of another embodiment of the electrode system of FIG. 6a, illustrating that the coupler/decoupler can be at different positions.

In some embodiments, the signals that flow through conductive lines 77, 78, and 79 flow through cable 31 through separate conductive lines, as shown in FIG. 5. The separate conductive lines are preferably insulated from each other and coupled together in a single cable to reduce the likelihood of them becoming tangled. The separate conductive lines are represented as cable 31 in FIGS. 1a and 1b for simplicity. In other embodiments, however, the signals flowing through conductive lines 78 and 79 flow through the same conductive line as shown in FIGS. 6a and 6b.

FIGS. 2a and 2b are side views of patient 15 corresponding to FIGS. 1a and 1b, respectively. In FIG. 2a, electrode pads 80 and 81 are in the anterior-anterior placement on patient 15 so there is an impedance $Z_0$ between them. Impedance $Z_0$ corresponds to the transthoracic and contact impedances and represents the impedance between pads 80 and 81 while they are coupled to patient 15. In FIG. 1a, connector 75 is not connected to connector 50 so signals flowing through patient 15 do not flow through electrode pad 82. Accordingly, it is not shown in FIG. 2a for simplicity. It should be noted that impedance $Z_0$ generally depends on the potential difference between pads 80 and 81.

In operation, signal $S_{Defib}$ is provided by source 12 and flows to pad 80 through cable 31 and conductive line 77, as shown in FIG. 2a. Signal $S_{Defib}$ flows through patient 15 and defibrillates his or her heart (not shown). Signal $S_{Defib}$ is attenuated by impedance $Z_0$ as it flows through patient 15 to pad 81. In response, signal $S_0$ is outputted through pad 81 where it flows through conductive line 78 and through connector 50 to cable 31. Signal $S_0$ then flows through cable 31 to connector 30 and physiological power source 12 to complete the circuit.

In FIG. 2b, electrode pads 80 and 81 are in the anterior-anterior placement on patient 15 and in communication with physiological power source 12 as described above. Electrode pad 82 is positioned on posterior 15b of patient 15 and connector 75 is connected to connector 50 (FIG. 1b) so pad 82 is in communication with physiological power source 12. Impedances $Z_1$, $Z_2$, and $Z_3$ correspond to the transthoracic and contact impedances and depend on the potential differences between pads 80, 81, and 82. Impedances $Z_1$, $Z_2$, and $Z_3$ represent the impedances between pads 80, 81, and 82 while they are coupled to patient 15.

Hence, there is an impedance $Z_1$ between electrode pads 80 and 81 and an impedance $Z_2$ between electrode pads 80 and 82. Further, there is an impedance $Z_3$ between electrode pads 81 and 82. It should be noted that the impedance between pads 80 and 81 in FIG. 2b is less than impedance $Z_0$ of FIG. 2a. This is because impedances $Z_1$, $Z_2$, and $Z_3$ are connected together in what is commonly referred to as a Delta configuration in the electrical arts and correspond to a series-parallel combination of impedances.

In operation, signal $S_{Defib}$ is provided by source 12 and flows to pad 80 through cable 31 and conductive line 77. Signal $S_{Defib}$ flows through patient 15 as shown in FIG. 2b and defibrillates his or her heart (not shown). Signal $S_{Defib}$ is attenuated by impedances $Z_1$, $Z_2$, and $Z_3$ as it flows through patient 15 to pads 81 and 82 as signals $S_1$ and $S_2$, respectively. In response, signals $S_1$ and $S_2$ flow through conductive lines 78 and 79, respectively, and connector 50 to cable 31. In this example, signals $S_1$ and $S_2$ flow separately (FIG. 5) through cable 31 to connector 30 and physiological power source 12 to complete the circuit. In other examples, however, they can flow together (FIGS. 6a and 6b) through cable 31 to connector 30.

As mentioned above, electrode pad 82 can have many different dimensions and shapes, such as pad 83. Hence, in another aspect of the invention, the dimension and shape of pad 82 is chosen to further reduce impedances $Z_1$, $Z_2$, and $Z_3$ by reducing the contact impedance between pad 82 and patient 15. By making the dimensions of pad 82 larger, these impedances are made smaller because the area of pad 82 is larger. By making the dimensions of pad 82 smaller, these impedances are made larger because the area of pad 82 is smaller.

It should be noted that, in FIGS. 1a and 2a, BLS is being provided to patient 15 and, in FIGS. 1b and 2b, ALS is being provided. Hence, another advantage of electrode system 40 is that the configuration of electrode pads can be changed quickly and efficiently between BLS and ALS. In the ALS configuration, connector 75 can be disconnected from connector 50 to provide BLS (FIG. 1a). This feature is useful because some responders may prefer to use two electrode pads in the configuration shown in FIGS. 1a and 2a instead of three as shown in FIGS. 1b and 2b. The BLS configuration is useful for lay people because it is simple and preferred by medical personnel in some instances. In other instances, the ALS configuration of FIGS. 1b and 2b is preferred.

FIG. 3 is a side view of patient 15 showing the electric field lines which extend through patient 15 when there is a potential difference between pads 80, 81, and 82. It should be noted that the electric field extending through a patient is sometimes referred to in the art as a bio-electric field. Electric field lines 66 extend between pads 80 and 81 in response to a potential difference therebetween; electric field lines 67 extend between pads 80 and 82 in response to a potential difference therebetween; and electric field lines 68 extend between pads 81 and 82 in response to a potential difference therebetween. There exists a region 65 of maximum electric field within patient 15 between pads 80, 81, and 82 and its position is adjustable by adjusting the potential difference between pads 80, 81, and 82. For example, region 65 can be moved towards and away from the heart (not shown) of patient 15. In this way, a desired defibrillation signal is provided to the heart of patient 15 to resuscitate him or her.

For example, as the potential difference between pads 80 and 81 increases, region 65 moves in a direction away from pad 82. As the potential difference between pads 81 and 82 increases, region 65 moves in a direction away from pad 80. As the potential difference between pads 80 and 82 increases, region 65 moves in a direction away from pad 81. In this way, region 65 can be moved to provide the heart of patient 15 with a desired defibrillation signal. This is useful because it has been well established, as discussed above, that different people have different transthoracic impedances so it is useful to move region 65 in response to the impedance of patient 15.

Figure 4A:
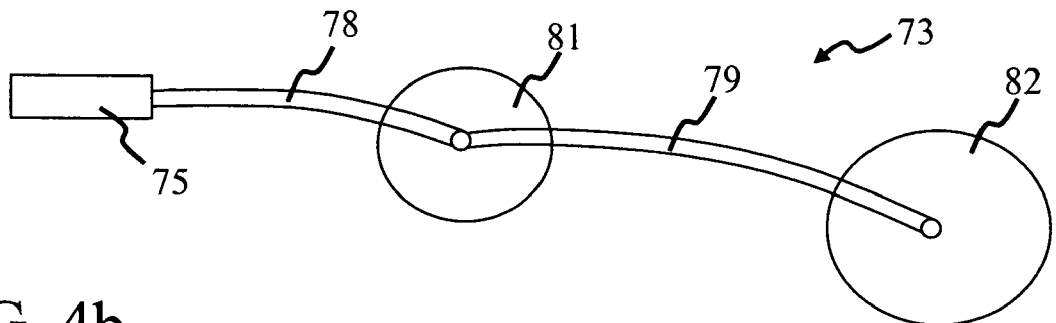
FIG. 4a is a top view of one embodiment of an electrode set, in accordance with the present invention.

FIG. 4a is a top view of one embodiment of an electrode set 73, which can be used with electrode system 40. Set 73 includes conductive line 78 with connector 75 coupled to one end and electrode pad 81 coupled to its other end. In this embodiment, conductive line 79 is also connected to electrode pad 81 at one end and electrode pad 82 at its other end so that electrode pads 81 and 82 are in communication with each other through conductive line 79.

Figure 4B:
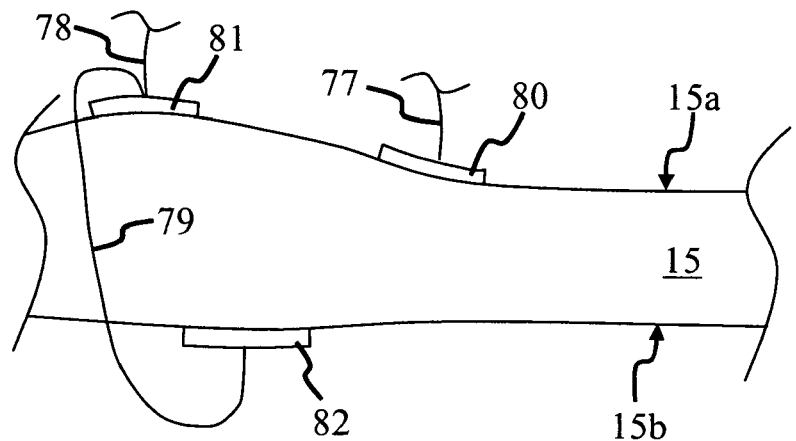
FIG. 4b is a side view of the electrode set of FIG. 4a coupled to the patient.

FIG. 4b is a side view of electrode set 73 coupled to patient 15. Electrode pad 80 is positioned in the anterior-apex position. Further, electrode set 73 is coupled to patient 15 so that electrode pads 81 and 82 are positioned in the anterior-sternum and posterior positions, respectively.

Figure 4C:
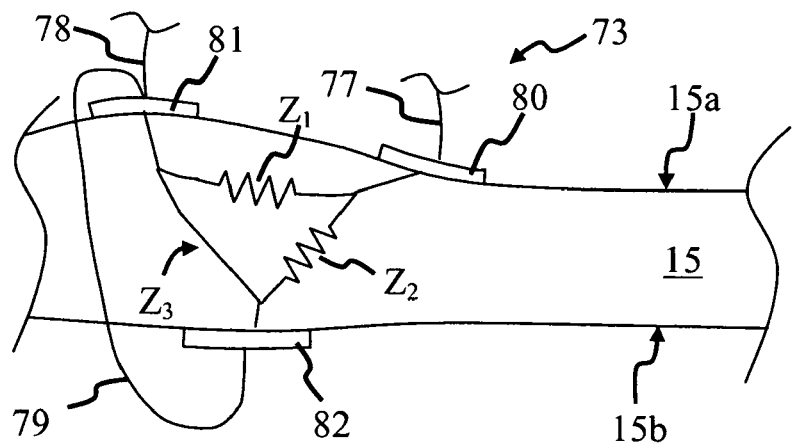
FIG. 4c is a side view of an electrode system, which includes the electrode set of FIG. 4a, coupled to a patient and showing the impedances between the electrode pads included therein.

FIG. 4c is a side view of electrode set 73 coupled to patient 15 showing the impedances between pads 80, 81, and 82 in the configuration shown in FIG. 4b. In this example, impedance $Z_1$ is that between pads 80 and 81 and impedance $Z_2$ is that between pads 80 and 82. Impedance $Z_3$ is the impedance of conductive line 79 between pads 81 and 82. Hence, impedance $Z_3$ is less than impedances $Z_1$ and $Z_2$ and is represented as a conductive line in FIG. 4c for simplicity. In this example, impedance $Z_3$ is what is often referred to in the electrical arts as a short circuit. In this configuration, the transthoracic impedance is represented by the parallel combination of impedances $Z_1$ and $Z_2$ because pads 81 and 82 are shorted together by conductive line 79.

FIG. 5 is a more detailed top view of electrode system 40 coupled to physiological power source 12. Electrode system 40 includes equipment side portion 41 coupled to patient side portion 42. In this embodiment, physiological stimulator includes a port 16 shaped and dimensioned to receive connector 30. Engagement elements 17, 18, and 19 extend from port 16 and are coupled to separate contacts of physiological power source 12. Connector 30 is repeatably moveable between engaged and disengaged positions with port 16.

Equipment side portion 41 includes connector 30 coupled to connector 50 through cable 31. Connector 30 includes a housing 32 which carries complementary engagement elements 33, 34, and 35. Complementary engagement elements 33, 34, and 35 are shaped and dimensioned to be received by engagement elements 17, 18, and 19, respectively. Connector 50 includes a housing 51 with ports 52 and 53 and engagement elements 54, 55, and 56. Engagement elements 54 and 55 extend from port 52 and engagement element 56 extends from port 53. Engagement elements 54, 55, and 56 are coupled to complementary engagement elements 33, 34, and 35, respectively, through conductive lines 36, 37, and 38, respectively. Conductive lines 36, 37, and 38 are included in cable 31 (FIGS. 1a and 1b).

In this embodiment, patient side portion 42 includes electrode sets 70 and 71. Electrode set 70 includes a connector 110 with a housing 72, which carries complementary engagement elements 73 and 74. Complementary engagement elements 73 and 74 are shaped and dimensioned to be received by engagement elements 54 and 55, respectively. Complementary engagement elements 73 and 74 are coupled to electrode pads 80 and 81, respectively, through corresponding conductive lines 77 and 78.

Electrode set 71 includes a connector 111 with housing 75, which carries a complementary engagement element 76. Complementary engagement element 76 is shaped and dimensioned to be received by engagement element 56 and is repeatably moveable between engaged and disengaged positions therewith. Complementary engagement element 76 is coupled to posterior electrode pad 82 through conductive line 79. Connectors 110 and 111, are shaped and dimensioned to be repeatably received by ports 52 and 53, respectively, and are repeatably moveable between engaged and disengaged positions therewith. It should be noted that engagement elements 17, 18, and 19, complementary engagement elements 33, 34, and 35, engagement elements 54, 55, and 56, and complementary engagement elements 73, 74, and 75 include electrically conductive material, such as copper.

In operation, connector 30 is engaged to port 16 so that engagement elements 17, 18, and 19 are engaged with complementary engagement elements 33, 34, and 35, respectively, and electrical signals can flow therebetween. Connector 110 is engaged to port 52 so that engagement elements 54 and 55 are engaged with complementary engagement elements 73 and 74, respectively, and electrical signals can flow therebetween. In this way, electrode pad 80 is in communication with physiological power source 12 through conductive lines 77, 36, and 13. Further, electrode pad 81 is in communication with physiological power source 12 through conductive lines 78, 37, and 14. Hence, electrode set 70 can be used as discussed in FIG. 1a.

If desired, electrode set 71 can be added to electrode system 40, as shown in FIG. 1b, by engaging connector 111 with port 53 so that engagement element 56 engages complementary engagement element 76 and electrical signals can flow therebetween. In this way, electrode pad 82 is in communication with physiological power source 12 through conductive lines 79, 38, and 15. In accordance with the invention, this can be done without decoupling electrode pads 80 and 81 from patient 15 and without disengaging connector 110 from port 52. Hence, electrode set 70 and 71 can be used as discussed in FIG. 2b.

It should be noted that in some embodiments, connectors 30 and 50 can be integrated together to form a single connector. Hence, equipment side portion 41 can be replaced by a connector 58 as indicated by substitution arrow 57. Connector 58 includes connector 50 with housing 51 which carries complementary engagement elements 33, 34, and 35. Complementary engagement elements 33, 34, and 35 are connected to engagement elements 54, 55, and 56 through conductive lines 36, 37, and 38, which are also carried by housing 51.

It should also be noted that electrode sets 70 and 71 are separate from each other so that they can be repeatably engaged and disengaged from connector 50 independently. However, they can be integrated together as in an electrode set 70'. In this embodiment, electrode set 70' includes a connector 110' with housing 72. Housing 72 carries complementary engagement elements 73, 74, and 76, which are connected to electrode pads 80, 81, and 82, respectively, through corresponding conductive lines 77, 78, and 79.

Electrode set 70 can also be separated so that electrode pads 80 and 81 can be repeatably engaged and disengaged from connector 50 independently of each other and electrode set 71. One example of this is electrode set 242, which can replace electrode set 70. Electrode set 242 includes conductive line 77 with electrode pad 80 connected at one end and a housing 272 connected at its other. It also includes conductive line 78 with electrode pad 81 connected at one end and a housing 273 connected at its other. Housings 272 and 273 carry complementary engagement elements 73 and 74, respectively.

FIG. 6a is a top view of an electrode system 40', similar to electrode system 40, coupled to physiological power source 12. In this example, electrode system 40' includes an equipment side portion 41' coupled to patient side portion 42. Here, physiological stimulator 11 includes port 16 which extends through its surface 25. Engagement elements 17 and 19 extend from port 16 and are coupled to separate contacts of physiological power source 12 through conductive lines 13 and 15, respectively.

In this example, equipment side portion 41' includes a connector 44 coupled to a connector 46 through a cable 45, which includes conductive lines 36 and 38. Connector 44 includes housing 32 which carries complementary engagement elements 33 and 35. Complementary engagement elements 33 and 35 are shaped and dimensioned to be received by engagement elements 17 and 19, respectively. Connector 46 includes housing 51 with ports 52 and 53 and engagement elements 54, 55, and 56, as well as a coupler/decoupler 150. Coupler/decoupler 150 is described in more detail below.

Engagement elements 54 and 55 extend from port 54 and engagement element 56 extends from port 53. Engagement element 54 is coupled to engagement element 33 through conductive line 36 and engagement elements 55 and 56 are coupled to separate conductive branches of coupler/decoupler 150. Another conductive branch of coupler/decoupler 150 is coupled to engagement element 35 through conductive line 38. In this example, patient side portion 42 includes electrode sets 70 and 71, as described with FIG. 5.

Figure 7:
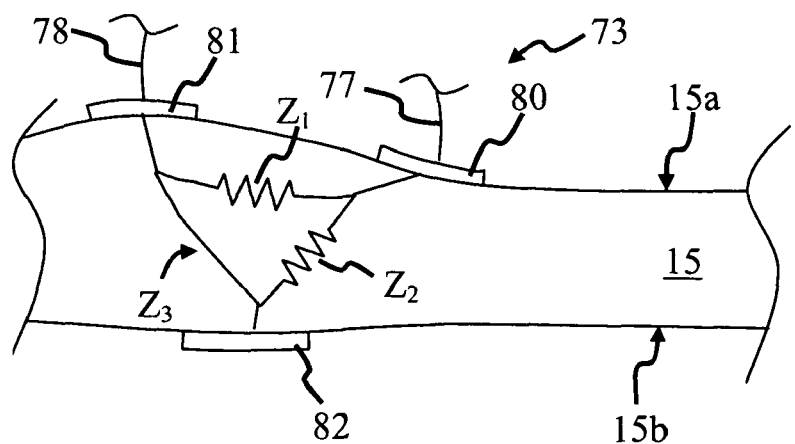
FIG. 7 is a side view of the electrode system of FIG. 6a coupled to the patient.

In operation, connector 44 is engaged to port 16 and connector 110 is engaged to port 52. In this way, electrode pad 80 is in communication with physiological power source 12 through conductive lines 77, 36, and 13. Further, electrode pad 81 is in communication with physiological power source 12 through conductive lines 78, 38, and 15, as well as coupler/decoupler 150. Hence, electrode set 70 can be used as shown in FIG. 2a. If desired, electrode set 71 can be added to electrode system 40' by engaging connector 111 with port 53 so that electrode pad 82 is in communication with physiological power source 12 through conductive lines 79, 38, and 15, as well as coupler/decoupler 150. In accordance with the invention, this can be done without decoupling electrode pads 80 and 81 from patient 15 and without disengaging connector 110 from port 52. Hence, electrode set 70 and 71 can be used as shown in FIG. 7, which is a side view of patient 15 with electrode pads 80, 81, and 82 coupled thereto as in FIG. 1b. Electrode pads 81 and 82 are shorted together and used in accordance with electrode system 40' of FIG. 6a.

In accordance with the invention, coupler/decoupler 150 couples signals flowing through engagement elements 55 and 56 towards physiological power source 12 together so that they flow through conductive line 38. Similarly, coupler/decoupler 150 decouples a signal flowing through conductive line 38 away from physiological power source 12 so that a portion of the signal flows through engagement element 55 and another portion flows through engagement element 56. In this way, coupler/decoupler 150 operates as a signal coupler and a signal decoupler.

In accordance with the invention, electrode pads 81 and 82 are in communication with each other through coupler/decoupler 150. Hence, signals that flow from respective electrode pads 81 and 82 are combined by coupler/decoupler 150 and flowed on conductive line 38 to physiological power source 12. Further, a signal that flows on conductive line 38 away from physiological power source 12 is decoupled by coupler/decoupler 150 so that a portion of it is provided to pad 81 and another portion is provided to pad 82. More information about coupler/decoupler 150 is provided with FIGS. 8a, 9a, 9b, and 9c.

It should be noted that connectors 44 and 46 can be integrated together to form a single connector. Hence, equipment side portion 41' can be replaced by a connector 61 as indicated by substitution arrow 60. Connector 61 includes connector 46 with housing 51 which carries complementary engagement elements 33 and 35. Complementary engagement element 33 is connected to engagement element 54 through conductive line 36 and engagement element 35 is connected to coupler/decoupler 150 through conductive line 38. In this example, conductive lines 36 and 38 are carried by housing 51.

FIG. 6b is a top view of other embodiments of equipment side portion 45 of FIG. 6a which show that coupler/decoupler 150 can be at different positions. In one embodiment, connector 46 is replaced with connector 47 as indicated by substitution arrow 120 where coupler/decoupler 150 is positioned outside of housing 51. In this example, coupler/decoupler 150 has separate conductive branches coupled to engagement elements 55 and 56 through conductive lines 58 and 59, respectively. Since coupler/decoupler 150 is positioned outside of housing 51, conductive lines 58 and 59 extend through it.

In another embodiment, equipment side portion 45 is replaced by electrode system 40 and coupler/decoupler 150 is positioned within physiological stimulator 11, as indicated by substitution arrow 121. Engagement elements 18 and 19 are connected to separate conductive branches of coupler/decoupler 150. Further conductive line 15 is connected to coupler/decoupler 150 so that signals flowing through engagement elements 18 and 19 towards physiological power source 12 are coupled together by coupler/decoupler 150 so that they flow through conductive line 15. Further, a signal flowing away from physiological power source 12 on conductive line 15 is decoupled by coupler/decoupler 150 so that a portion flows through engagement element 18 and another portion flows through engagement element 19.

FIGS. 8a and 8b are top views of different embodiments of coupler/decoupler 150 and coupler/decoupler 150', respectively, in accordance with the present invention. Coupler/decouplers 150 and 150' each include a conductive branch 151 and conductive branches 152 and 153 which extend at an angle therefrom so that coupler/decouplers 150 and 150' have a Y-shape. It should be noted that coupler/decouplers 150 and 150' can have other shapes which are not shown for simplicity. For example, coupler/decouplers 150 and 150' each include two conductive branches which extend from conductive branch 151 for illustrative purposes. In other example, however, they can have more than two conductive branches.

Conductive branch 151 is coupled to conductive branches 152 and 153 at one end and includes a proximal signal port 254 at its other end. In this example, proximal signal port 254 is at a coupled end 154 of coupler/decoupler 150 and 150'. Conductive branches 152 and 153 have ends coupled to conductive branch 151 and include distal signal ports 255 and 256, respectively, at their other ends. In this example, distal signal ports 255 and 256 are at decoupled ends 155 and 156, respectively, of coupler/decoupler 150 and 150'.

Coupler/decouplers 150 and 150' can include many different conductive materials typically used in physiological stimulator cables. Some suitable materials include copper and copper alloys, but there are others. An example of a copper alloy is silver plated bronze. Coupler/decouplers 150 and 150' are capable of flowing voltage and current signals typically provided by physiological power sources, such as source 12. A voltage signal from an AED typically has a voltage amplitude between about 500 volts to about 3200 volts and a current signal from an AED typically has a current amplitude between about 0.5 Amps to about 60 Amps. A current signal from an external pacer typically has a current amplitude of about 100 milliamps to about 200 milliamps. Coupler/decouplers 150 and 150' can also include a single piece of conductive material or separate pieces connected together. The separate pieces can be connected together in many different ways, such as by welding, soldering, and/or crimping.

In operation, a signal $S_3$ flowing into coupled end 154 is outputted through decoupled ends 155 and 156 as signals $S_4$ and $S_5$, respectively. Further, signals $S_4$ and $S_5$ flowing into decoupled ends 155 and 156, respectively, are outputted through coupled end 154 as signal $S_3$. In this way, coupler/decoupler 150 and 150' operate as a signal coupler and a signal decoupler.

In accordance with the invention, signal $S_3$ flows between coupler/decoupler 150 and a physiological power source (not shown). Further, signals $S_4$ and $S_5$ flow between coupler/decoupler 150 and an electrode system (not shown). In this way, and as will be discussed in more detail below, coupler/decoupler 150 combines signals $S_4$ and $S_5$ flowing to the physiological power source to provide signal $S_3$ and separates signal $S_3$ flowing away from it to provide signals $S_4$ and $S_5$.

Figure 10:
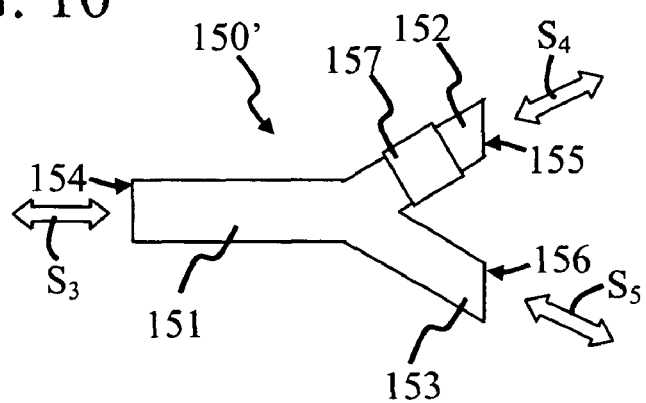
FIG. 10 is an embodiment of another coupler/decoupler, in accordance with the present invention.

In FIG. 8*b*, coupler/decoupler 150' has a similar structure to coupler/decoupler 150 and operates in much the same way. One difference, however, is that it includes electronic devices 157 and 158 in conductive branches 152 and 153, respectively. Electronic devices 157 and 158 can be of many different types. For example, they can be variable impedance devices, switches, or combinations thereof. It should be noted that in other examples, coupler/decoupler 150' can include only one electronic device in one branch, as shown in FIG. 10. However, in this example branches 152 and 153 each include one electronic device for illustrative purposes.

When devices 157 and 158 include switches, they are useful to control the flow of signals $S_4$ and $S_5$ through branches 152 and 153, respectively. In accordance with the invention, when device 157 is a switch that is activated and device 158 is a switch that is deactivated, signal S4 is the same as signal $S_3$. Similarly, when device 157 is a switch that is deactivated and device 158 is a switch that is activated, signal $S_5$ is the same as signal $S_3$. In this way, the flow of signals S4 and $S_5$ through branches 152 and 153, respectively, is controllable.

In accordance with the invention, when devices 157 and 158 include variable impedance devices, they are useful to adjust the impedance of branches 152 and 153, respectively, relative to each other and branch 151. In this way, the signal amplitude ratio between signals S4 and $S_5$ can be adjusted relative to each other and to signal S3. For example, when the impedance of device 157 is made larger and the impedance of device 158 is left the same, signal $S_5$ increases in amplitude and signal S4 decreases in amplitude. When the impedance of device 157 is made smaller and the impedance of device 158 is left the same, signal $S_4$ increases in amplitude and signal $S_5$ decreases in amplitude. Similarly, when the impedance of device 158 is made larger and the impedance of device 157 is left the same, signal S4 increases in amplitude and signal $S_5$ decreases in amplitude. When the impedance of device 158 is made smaller and the impedance of device 157 is left the same, signal $S_5$ increases in amplitude and signal $S_4$ decreases in amplitude.

In this way, the impedance between branches 152 and 153 is adjustable and the amplitudes of signals $S_3$, $S_4$, and $S_5$ are adjustable in response. In general, if device 157 is a variable impedance device and its impedance increases, then the amplitude of signal $S_4$ decreases. Further, if device 157 is a variable impedance device and its impedance decreases, then the amplitude of signal $S_4$ increases. Similarly, if device 158 is a variable impedance device and its impedance increases, then the amplitude of signal $S_5$ decreases. Further, if device 158 is a variable impedance device and its impedance decreases, then the amplitude of signal $S_5$ increases. In this way, coupler/decoupler 150' operates as a variable impedance device.

FIGS. 9*a*, 9*b*, and 9*c* are more detailed views of one embodiment of connector 46, in accordance with the present invention. FIG. 9*a* is a top view of connector 46. FIG. 9*b* is a side view of connector 46 taken along a cut-line 9*b*-9*b'* of FIG. 9*a* and FIG. 9*c* is a side view of connector 20 taken along a cut-line 9*c*-9*c'*. In this embodiment, connector 46 includes coupler/decoupler 150 housed within housing 51. Engagement element 56 is coupled to decoupled end 155 and engagement element 55 is coupled to decoupled end 156 through respective conductive lines 160 and 161.

FIG. 10 is an embodiment of coupler/decoupler 150' in which branch 152 includes electronic device 157 and branch 153 does not include electronic device 158. In this particular example, electronic device 157 includes a voltage controlled electronic switch. A voltage controlled electronic switch is one that is activated and deactivated in response to a voltage signal. The switch is a spark gap device, but it could be another type of switch, such as a high power transistor, in other examples. Further, in other examples, the switch can be current controlled instead of voltage controlled. A current controlled electronic switch is one that is activated and deactivated in response to a current signal.

A spark gap device has contacts spaced apart by a gap in an otherwise closed electric circuit. One example of a spark gap device is provided by Siemens AG, which makes a Siemens spark voltage protector (SVP). A charge flow occurs between the gap when the potential difference between the contacts is above a predetermined voltage level. As will be discussed in more detail below, the spark gap device is useful to control the flow of the monitoring, pacing, and defibrillation signals through coupler/decoupler 150' and electrode pads 80, 81, and 82. This can be done because the monitoring, pacing, and defibrillation signals each have different signal voltage amplitudes which can activate and deactivate the spark gap device.

For example, the monitor and pacing signals each have a voltage amplitude that is less than the predetermined voltage level so that the spark gap device is deactivated in response to them and there is no charge flow in the gap between the contacts. The defibrillation signal, however, has a voltage amplitude that is greater than the predetermined voltage level so that the spark gap device is activated in response to it and there is a charge flow between the contacts in the gap.

Hence, when the potential difference between the contacts is above the predetermined voltage level, the spark gap device will flow charge in the gap to provide a low impedance current path within the gap so that the potential difference between the contacts is driven to a low impedance value. When the potential difference between the contacts is below the predetermined voltage level, the spark gap device will not flow a charge in the gap and there will be a high impedance current path within the gap so that the potential difference between the contacts is driven to a high impedance value. In one example, the low impedance value is within a range from less than one ohm to about ten ohms and the high impedance value is in a range from about 100 kiloohms to about one megaohms. It should be noted, however, that the high and low impedance values can be outside of these ranges, which are provided for illustrative purposes.

Figure 11A:
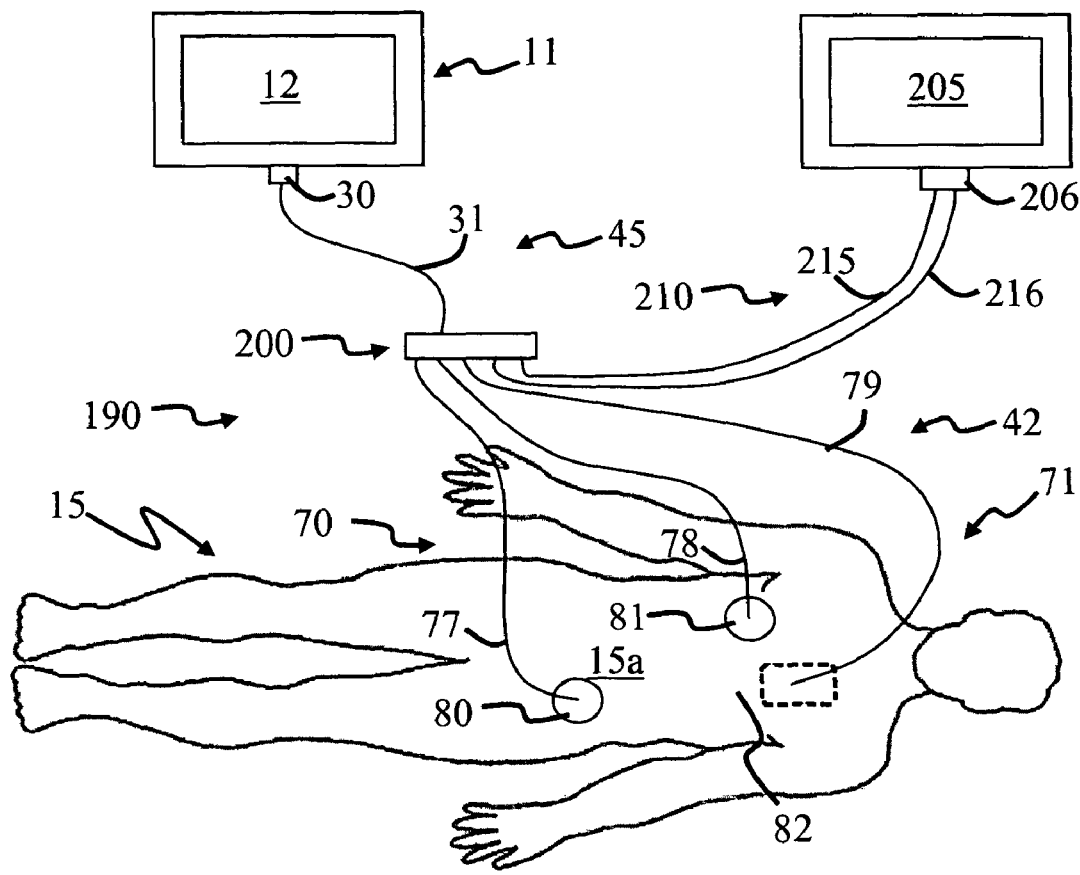
FIG. 11a is a top view of two physiological stimulators coupled to a patient through an electrode system, in accordance with the present invention.
Figure 11B:
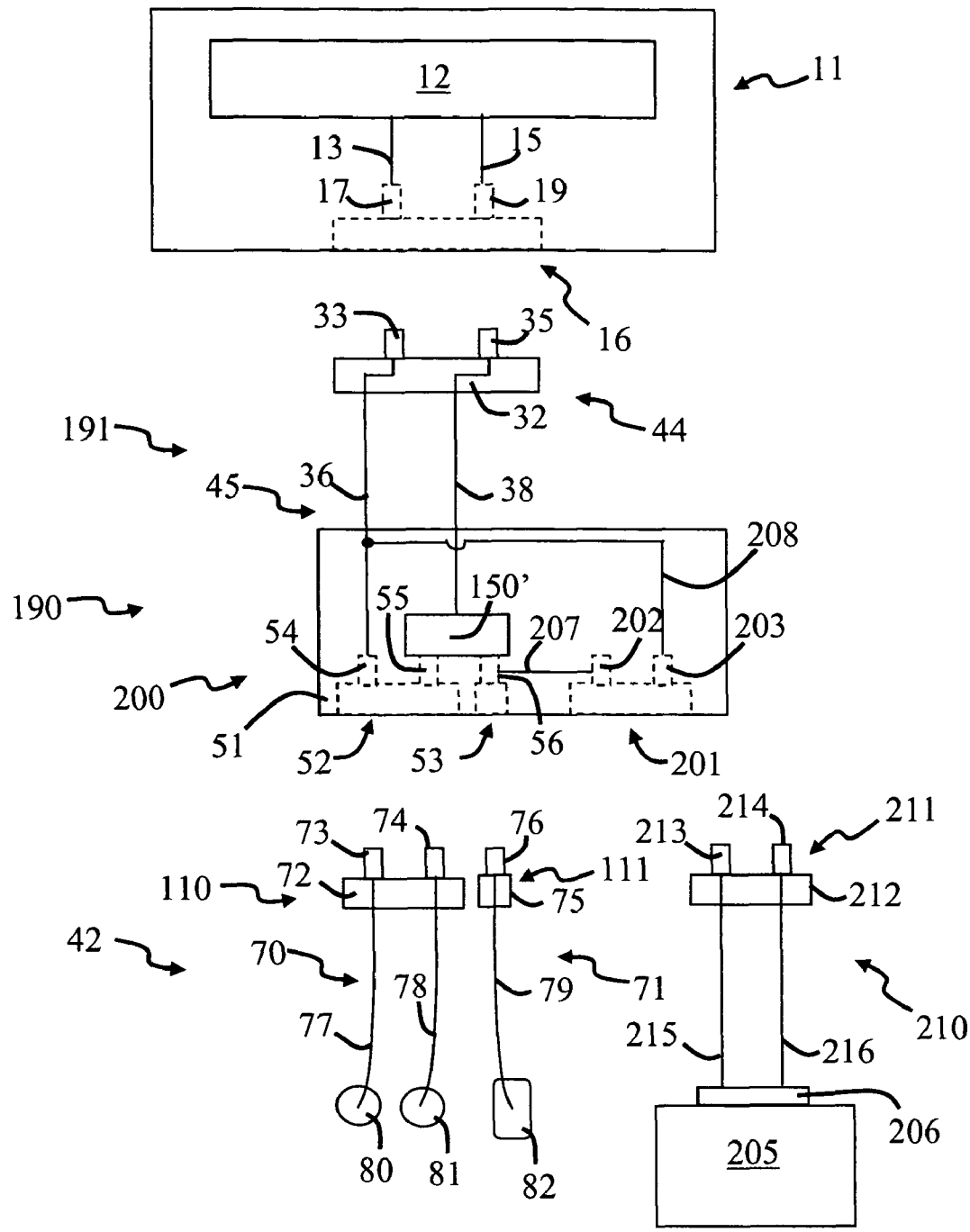
FIG. 11b is a more detailed top view of the electrode system of FIG. 11a, in accordance with the present invention.
Figure 11C:
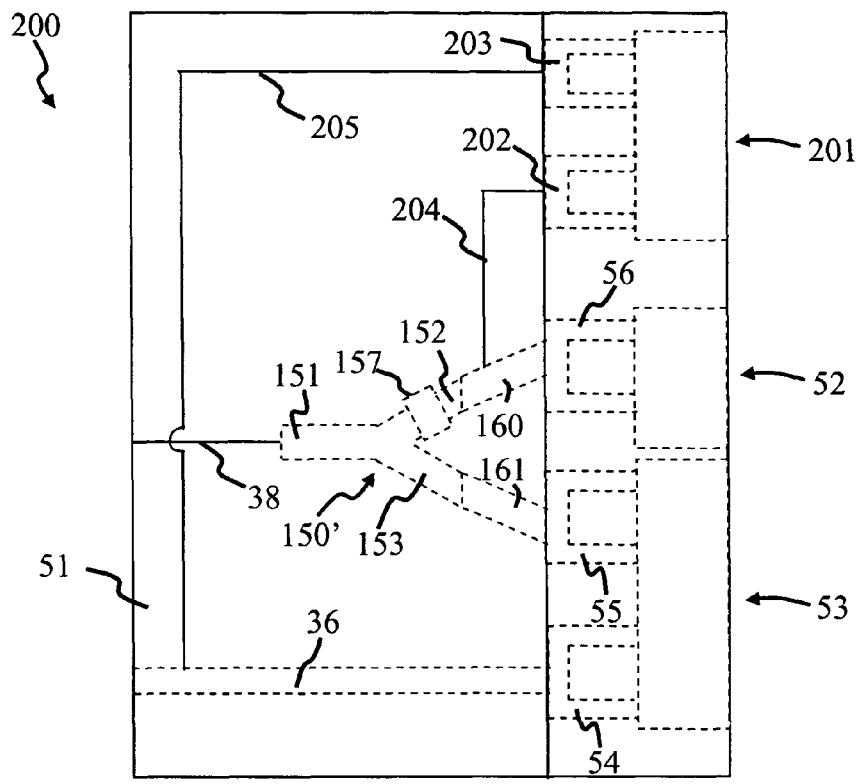
FIG. 11c is a top view of a connector, in accordance with the present invention, included in the electrode system of FIGS. 11a and 11b.

FIG. 11a is a top view of physiological stimulator 11 and a physiological stimulator 205 coupled to patient 15 through an electrode system 190 and a cable system 210, in accordance with the present invention. FIG. 11b is a more detailed top view of electrode system 190 and cable system 210 and FIG. 11c is a more detailed top view of a connector 200 included in electrode system 190 of FIGS. 11a and 11b.

Electrode system 190 is useful in situations in which patient 15 is being paced using a pacing signal provided by physiological stimulator 11, but it is desirable to pace him or her with a pacing signal provided by physiological stimulator 205 instead. In these situations, it is desirable to replace stimulator 11 with stimulator 205. These situations generally occur when transferring the care of patient 15 from the medical equipment of one emergency responder to that of another. It is often desired to reduce the amount of time the pacing is stopped when transferring patient 15. In this way, the need for pacing recapture is reduced and, as a result, it is less likely that the patient's health will be negatively impacted. It should be noted that it is generally desirable to stop the pacing when electrode pad 82 is coupled to posterior 15b of patient 15. This is to reduce the likelihood of having the pacing signal flow through the person coupling pad 82 to patient 15.

In this embodiment, electrode system 190 includes an equipment side portion 191 and patient side portion 42. Equipment side portion 191 includes cable 45 coupled between connector 44 and a connector 200. Physiological stimulator 205 is connected to connector 200 through cable system 210 and is connected to patient 15 through patient side portion 42.

In this example and as shown in FIG. 11b, connector 200 includes the structure of connector 46, as described in FIG. 6a, except coupler/decoupler 150 is replaced by coupler/decoupler 150', as described with FIG. 10. In accordance with the invention, connector 200 also includes a port 201 shaped and dimensioned to receive a connector 211 of cable system 210, which is described below. Complementary engagement elements 202 and 203 extend from port 201. Engagement element 202 is connected to engagement element 56 through a conductive line 207 and engagement element 203 is connected to conductive line 36 through a conductive line 208.

Cable system 210 includes conductive lines 215 and 216, which extend between a connector 206 and connector 211. Connector 211 includes a housing 212 which carries complementary engagement elements 213 and 214. Complementary engagement elements 213 and 214 are shaped and dimensioned to be received by engagement elements 202 and 203, respectively, when port 201 receives connector 211. Physiological stimulator 205 is in communication with engagement elements 54 and 56 when stimulator 205 is connected to connector 206 and port 201 receives connector 211. In this embodiment, patient side portion 42 includes electrode sets 70 and 71 connected to ports 52 and 53 of connector 200.

In one mode of operation, connectors 44 and 110 are engaged to ports 16 and 52, respectively. In this way, electrode pad 80 is in communication with physiological power source 12 through conductive lines 77, 36, and 13. Further, electrode pad 81 is in communication with physiological power source 12 through conductive lines 78, 38, and 15, as well as coupler/decoupler 150'. Patient 15 is paced with the pacing signal from physiological stimulator 11 provided to patient 15 through electrode pads 80 and 81.

Electrode set 71 is added to electrode system 190 by engaging connector 111 with port 53 so that electrode pad 82 is in communication with physiological power source 12 through conductive lines 79, 38, and 15, as well as coupler/decoupler 150'. The pacing signal from stimulator 11 is stopped and electrode pad 82 is coupled to posterior 15b of patient 15. The pacing signal from stimulator 11 is then restarted.

Connector 211 is coupled to port 201 so that physiological stimulator 205 is in communication with patient 15 through pads 80 and 82 as described with FIG. 11b. The pacing signal from physiological stimulator 205 is then provided to patient 15 through electrode pads 80 and 82 and the pacing of patient 15 with the pacing signal from stimulator 11 is discontinued. One way the pacing signal from stimulator 11 is discontinued is by switching off physiological stimulator 11.

The pacing signal from physiological stimulator 205 flows through conductive line 216 to conductive line 208, where it then flows to conductive line 77 and pad 80. The pacing signal from physiological stimulator 205 flows through patient 200 to pad 82 and conductive line 79. It then flows to physiological stimulator 205 through conductive lines 207 and 215 to complete the circuit.

If the pacing signal from stimulator 205 is pacing patient 15, then connector 44 is disconnected from physiological stimulator 11. If the pacing signal from stimulator 205 is not pacing patient 15, then the pacing signal from stimulator 11 is restarted. One way the pacing signal from stimulator 11 is restarted is by switching on physiological stimulator 11. These steps can be repeated until patient 15 is being paced with the pacing signal from stimulator 205.

In this way, connector 200 allows patient 15 to be transferred from the physiological stimulator of one medical responder to that of another while still being paced. Also, connector 200 reduces the likelihood of the pacing being undesirably stopped. Further, connector 200 allows patient 15 to be paced with a pacing signal flowing between electrode pads 80 and 81 as well as one flowing between electrode pads 80 and 82.

Figure 12A:
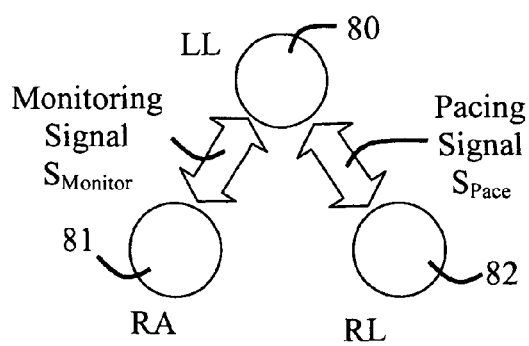
FIGS. 12a and 12b are diagrams showing examples of the flow of the monitoring, pacing, and defibrillation signals using the electrode system of FIGS. 11a and 11b.
Figure 12B:
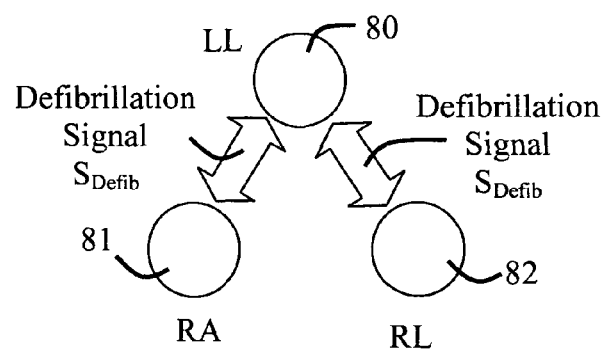

FIGS. 12a and 12b are diagrams of the flow of the pacing, defibrillation, and monitoring signals between electrode pads 80, 81, and 82 using electrode system 190 of FIGS. 11a and 11b. It should be noted that in FIGS. 12a and 12b, LL, RA, and RL denote "left leg", "right arm", and "right leg", respectively, which is a convention generally used in the medical art. In one mode of operation, the pacing signal from physiological stimulator 205, denoted as $S_{pace}$, is flowed between pads 80 and 82, as described above, while monitoring signal $S_{Monitor}$ is flowed between pads 80 and 81 (FIG. 12a). In this way, monitoring signal $S_{Monitor}$ is more isolated from corruption by pacing signal $S_{pace}$ so that patient 15 is more effectively monitored. Hence, separate monitoring electrode pads need not be applied to patient 15 for ECG monitoring. This reduces the number of electrode pads used to monitor, defibrillate, and/or pace patient 15 and allows patient 15 to be monitored while being demand paced. Further, posterior electrode 82 may be used as an ECG monitor reference electrode to implement classical three electrode ECG monitoring to these procedures, which is well-known in the medical art. Single lead ECG monitoring. This will further enhance the quality of ECG monitoring during resuscitation. In another mode of operation, defibrillation signal $S_{Defib}$ is flowed between pads 80 and 81 and between pads 80 and 82 (FIG. 12b), because electronic device 157 is activated in response to defibrillation signal $S_{Defib}$ since it includes the spark gap device. In this way, the impedance of patient 15 is reduced since pads 81 and 82 are shorted together and more effective defibrillation can be provided.

Figure 11D:
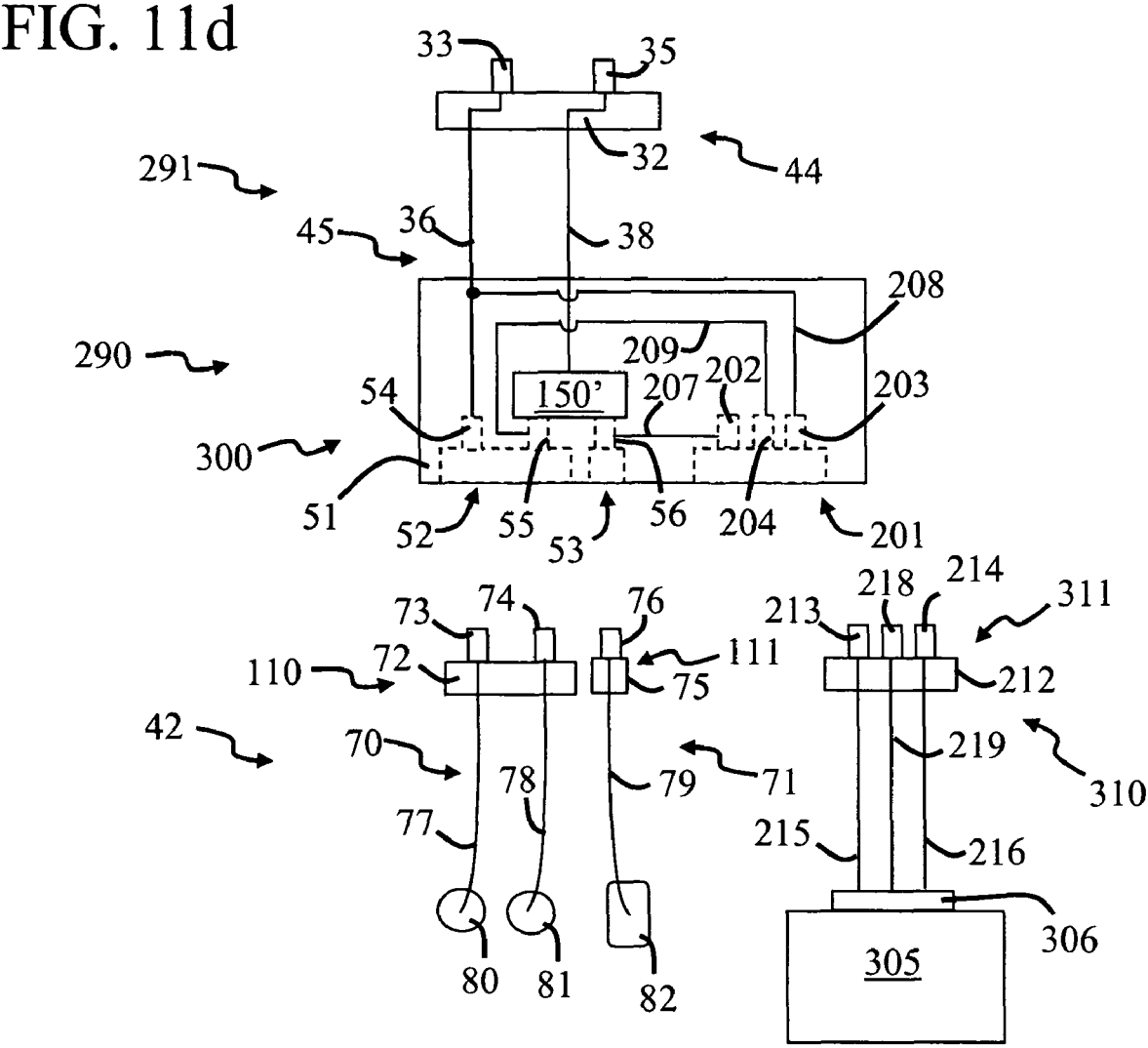
FIG. 11d is a more detailed top view of another embodiment of an electrode system, in accordance with the present invention.

FIG. 11*d* is a more detailed top view of an electrode system 290 and a monitor 305 coupled together through a cable system 310, in accordance with the present invention. Monitor 305 can be the same or similar to those mentioned above. Electrode system 290, cable system 310, and monitor 305 can replace electrode system 190, cable system 210, and physiological stimulator 205, respectively, as shown in FIGS. 11*a* and 11*b* above. In discussed in more detail below, electrode system 290, cable system 310, and monitor 305 are useful to provide three electrode monitoring of patient 15.

In one example, electrode system 290 includes an equipment side portion 291 and patient side portion 42. Equipment side portion 291 includes cable 45 coupled between connector 44 and a connector 300. Physiological stimulator 205 is connected to connector 300 through cable system 310 and is connected to patient 15 through patient side portion 42, as discussed below.

In this example, connector 300 includes the structure of connector 200, as described in FIG. 11*b*. In accordance with the invention, connector 300 also includes port 201 shaped and dimensioned to receive a connector 311 of cable system 310. Engagement elements 202, 203, and 204 extend from port 201. Engagement element 202 is connected to engagement element 56 through conductive line 207 and engagement element 203 is connected to conductive line 36 through conductive line 208. Engagement element 204 is connected to engagement element 55 through a conductive line 209.

Cable system 310 includes conductive lines 215, 216, and 217, which extend between a connector 306 and connector 311. Connector 311 includes housing 212 which carries complementary engagement elements 213, 214, and 218. Complementary engagement elements 213, 214, and 218 are shaped and dimensioned to be received by engagement elements 202, 203, and 204, respectively, when port 201 receives connector 311. Monitor 305 is in communication with engagement elements 54, 55, and 56 when monitor 305 is connected to connector 306 and port 201 receives connector 311. In this example, patient side portion 42 includes electrode sets 70 and 71 connected to ports 52 and 53 of connector 300.

In operation, connectors 44 and 110 are engaged to ports 16 and 52, respectively, of physiological stimulator 11 (FIG. 11*b*). In this way, electrode pad 80 is in communication with physiological power source 12 through conductive lines 77, 36, and 13. Further, electrode pad 81 is in communication with physiological power source 12 through conductive lines 78, 38, and 15, as well as coupler/decoupler 150'. Electrode set 71 is added to electrode system 190 by engaging connector 111 with port 53 so that electrode pad 82 is in communication with physiological power source 12 through conductive lines 79, 38, and 15, as well as coupler/decoupler 150'. Connector 311 is coupled to port 201 so that monitor 305 is in communication with patient 15 through pads 80, 81, and 82 as described above.

In one mode of operation, patient 15 is monitored with monitoring signal $S_{Monitor}$ from monitor 305 provided to patient 15 through electrode pads 80 and 81. Monitoring signal $S_{Monitor}$ flows through conductive line 216 to conductive line 208, where it then flows to conductive line 77 and pad 80. Monitoring signal $S_{Monitor}$ then flows through patient 15 to pad 81 and conductive line 78. It then flows to monitor 305 through conductive lines 209 and 215 to complete the circuit.

In accordance with the invention, physiological stimulator 306 also flows a reference signal to conductive line 207 through conductive line 215. The reference signal flows through conductive line 207 to conductive line 79 and posterior electrode pad 82. The reference signal provides a reference potential for monitoring signal $S_{Monitor}$ flowing between electrode pads 80 and 81. The reference signal also provides patient 15 with a reference potential so that changes in his or her charge are reduced. One advantage is that more stable monitoring is provided because monitoring signal $S_{Monitor}$ is attenuated and distorted less as it flows through patient 15. As a result, its signal-to-noise ratio is higher then in situations where the reference signal is not provided. In this way, the monitoring signal is determined more accurately by monitor 305 after it flows through patient 15.

Figure 12C:
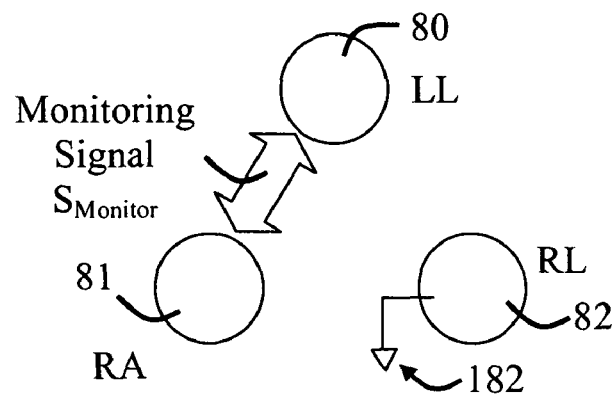
FIG. 12c is a diagram showing one example of the flow of the monitoring signal using the electrode system of FIG. 11d.

FIG. 12*c* is a schematic view of the flow of the monitoring signals between electrode pads 80 and 81 using electrode system 290, cable system 310, and physiological stimulator 306 as described in FIG. 11*d*. As described above, monitoring signal $S_{Monitor}$ flows between electrode pads 80 and 81 and electrode pad 82 is provide with a reference potential.

Figure 13:
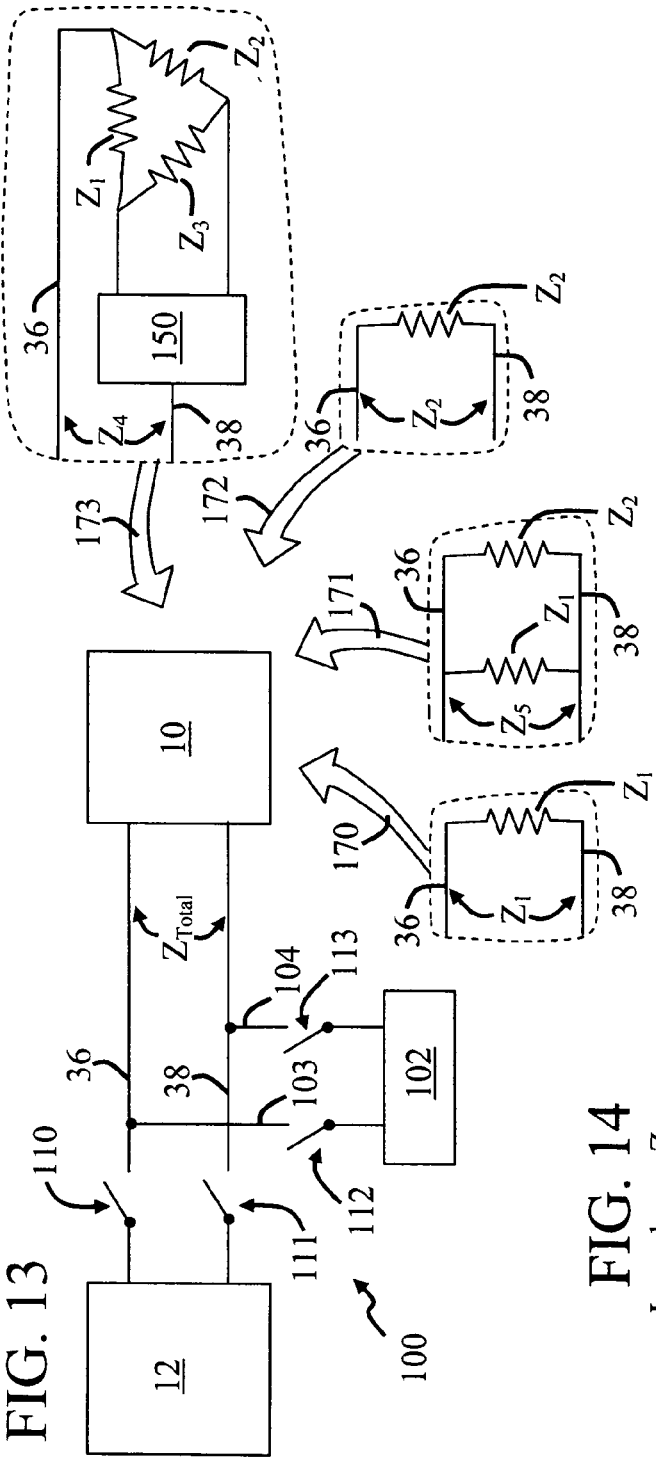
FIG. 13 is a block diagram of one embodiment of an impedance sensing circuit which can be included in a physiological stimulator, in accordance with the present invention.

FIG. 13 is a block diagram of one embodiment of an impedance sensing circuit 102 which can be included in physiological stimulator 11. Impedance sensing circuit 102 is useful to determine the impedance of patient 15 through the electrode system coupling patient 15 to physiological power source 12. This is useful to determine which electrode sets are coupled to patient 15. The impedance of patient 15 and the electrode system is represented in FIG. 13 as an impedance network 10 for simplicity and ease of discussion.

In this example, physiological stimulator power source 12 is coupled to impedance network 10 through conductive lines 36 and 38. Switches 110 and 111 are in series with conductive lines 36 and 38, respectively, and positioned between physiological power source 12 and network 10. Impedance sensing circuit 102 is coupled to conductive lines 36 and 38 with conductive lines 103 and 104, respectively. Conductive lines 103 and 104 are coupled to conductive lines 36 and 38, respectively, between network 10 and corresponding switches 110 and 111. The impedance between conductive lines 36 and 38 is represented as impedance $Z_{Total}$.

In a first mode of operation, switches 112 and 113 are activated and switches 103 and 104 are deactivated so that source 12 is in communication with network 10 and circuit 102 is not. In the first mode of operation, source 12 can provide the monitoring, pacing, and/or defibrillation signals to network 10 through conductive lines 36 and 38. In a second mode of operation, switches 112 and 113 are activated and switches 103 and 104 are deactivated so that circuit 102 is in communication with network 10 and physiological power source 12 is not. In the second mode of operation, circuit 102 can determine impedance $Z_{Total}$.

Impedance $Z_{Total}$, as determined by impedance sensing circuit 102, depends on many different factors. One factor is the transthoracic impedance of patient 15 and another factor is the contact impedance between patient 15 and the electrode pads coupled to him or her. Further, impedance $Z_{Total}$ also depends on the number and placement of the electrode pads coupled to patient 15 and conductive lines 36 and 38. The electrode system in this example is electrode system 401 of FIG. 6*a*, although the other electrode systems included herein could be used.

Impedance $Z_{Total}$ can be determined in many different ways by circuit 102. For example, it can be determined by providing a sensing signal and measuring the impedance in response. There are several different impedance measuring circuits know in the art that can be included in impedance sensing circuit 102. Some examples of impedance measuring circuits are discussed in U.S. Pat. Nos. 4,840,177 and 4,328,808, both of which are incorporated herein by reference.

In one example, if impedance sensing circuit 102 determines that impedance $Z_{Total}$ is $Z_O$, then electrode pads 80 and 81 are coupled to patient 15 as shown in FIGS. 1a and 2a and network 10 is the circuit indicated by a substitution arrow 170. If impedance sensing circuit 102 determines that impedance $Z_{Total}$ is impedance $Z_4$, then electrode pads 80, 81, and 82 are coupled to patient 15 as in FIGS. 1b and 2b and circuit 10 is as indicated by a substitution arrow 173. Impedance $Z_4$ includes a series-parallel combination of impedances $Z_1$, $Z_2$, and $Z_3$, as well as the impedance of coupler/decoupler 150. In other examples, coupler/decoupler 150 is replaced with coupler/decoupler 150' so that impedance $Z_4$ also includes the impedance of electronic devices 157 and 158.

If impedance sensing circuit 102 determines that impedance $Z_{Total}$ is impedance $Z_2$, then circuit 10 is as indicated by a substitution arrow 172. Here, electrode pads 80 and 82 are coupled to patient 15 and electrode pad 81 is not. If impedance sensing circuit 102 determines that impedance $Z_{Total}$ is impedance $Z_5$, then electrode pads 80 and 82 are coupled to patient 15 and circuit 10 is as indicated by a substitution arrow 172. Impedance $Z_5$ is the parallel combination of impedances $Z_1$ and $Z_2$, as shown in FIGS. 4b and 4c. In this way, circuit 102 can determine the configuration of the electrode pads that are coupled to patient 15.

It should be noted that if impedance sensing circuit 102 determines that impedance $Z_{Total}$ is above a predetermined value $Z_{Open}$, then electrode pads 80, 81, and 81 are not coupled to patient 15. This means that a signal provided by physiological power source 12 will not flow through electrode pads 80, 81, and/or 82 since the circuit between them and patient 15 is not complete. If impedance sensing circuit 102 determines that impedance $Z_{Total}$ is below a predetermined value $Z_{Short}$, then electrode pads 80, 81, and 81 are shorted together. This means that a signal provided by physiological power source 12 will flow mostly through electrode pads 80, 81, and/or 82 instead of patient 15.

It should also be noted that impedances $Z_{Open}$, $Z_{Short}$, $Z_1$, $Z_2$, and $Z_3$ can have many different values. Further, as mentioned above, it is well-known that a person's transthoracic impedance depends on a number of different factors, such as weight and skin type. It is also well known that the transthoracic impedance depends on the properties of the signal used to determine it. The signal properties can include its signal amplitude and frequency, for example, among others.

In one example, impedances $Z_O$, $Z_1$, $Z_2$, and $Z_3$ each have values of about 75Ω and impedances $Z_{Open}$ and $Z_{Short}$ each have values of about 1 MΩ and 10Ω, respectively. However, in other examples, impedances $Z_O$, $Z_1$, $Z_2$, $Z_3$, $Z_{Open}$ and $Z_{Short}$ can correspond to a range of impedance values. For example, impedances $Z_O$, $Z_1$, $Z_2$, and $Z_3$ can each have values of in a range from about 50Ω to 150Ω. Impedance $Z_{Open}$ can be in a range from about 100 kΩ to about 1 MΩ or greater. Further, impedance $Z_{Short}$ can have values from about 100Ω to 1Ω or less. It should be noted that these values and ranges for impedances $Z_O$, $Z_1$, $Z_2$, $Z_3$, $Z_{Open}$ and $Z_{Short}$ are provided for illustrative purposes and that impedances $Z_O$, $Z_1$, $Z_2$, $Z_3$, $Z_{Open}$ and $Z_{Short}$ can have different values and ranges.

Figure 14:
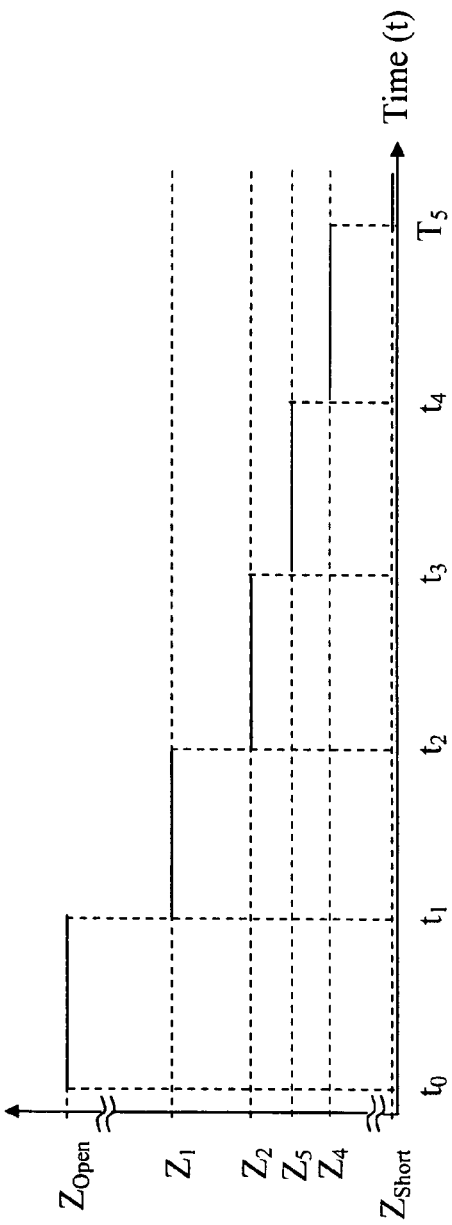
FIG. 14 is a graph showing impedance $Z_{Total}$ as a function of time t as determined by the impedance sensing circuit of FIG. 13.

FIG. 14 is a graph showing impedance $Z_{Total}$ as a function of time t. At a time $t_0$, electrode pads 80, 81, and 82 are not coupled to patient 15 so impedance $Z_{Total}$ is impedance $Z_{Open}$. At a time $t_1$, electrode pads 80 and 81 are coupled to patient 15 in the anterior-anterior placement so that impedance $Z_{Total}$ is impedance $Z_1$. Impedance $Z_1$ is less than impedance $Z_{Open}$. At a time $t_2$, electrode pads 80 and 82 are coupled to patient 15 in the anterior-posterior placement so that impedance $Z_{Total}$ is impedance $Z_2$. Impedance $Z_2$ is less than impedance $Z_1$. At a time $t_3$, electrode pads 80, 81, and 82 are coupled to patient 15 as shown in FIGS. 4c and 7 so that pads 81 and 82 are shorted together and impedance $Z_{Total}$ is impedance $Z_5$. Impedance $Z_5$ is less than impedance $Z_2$. At a time $t_4$, electrode pads 80, 81, and 82 are coupled to patient 15 so that impedance $Z_{Total}$ is impedance $Z_4$. Impedance $Z_4$ is less than impedance $Z_5$. At a time $t_5$, electrode pads 80, 81, and 82 are shorted together so that impedance $Z_{Total}$ is impedance $Z_{Short}$. Impedance $Z_{Short}$ is less than impedance $Z_4$. It should be noted that in this example, time $t_0$, $t_1$, $t_2$, $t_3$, $t_4$, and $t_5$ occur sequentially for illustrative purposes.

Figure 15A:
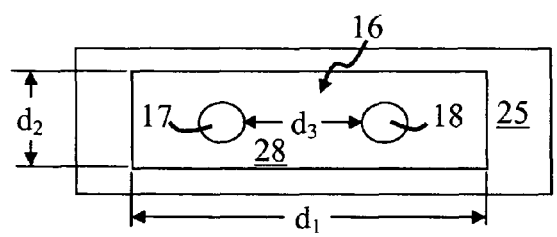
FIG. 15a is a view of the physiological stimulator of FIG. 6a taken along a cut line 15a-15a'.

FIG. 15a is a view of a physiological stimulator 11 taken along a cut line 15a-15a' of FIG. 6a. Port 16 has a rectangular shape with a length dimension of $d_1$ and a width dimension of $d_2$. Port 16 extends through a surface 25 of physiological stimulator 11 and engagement elements 17 and 18 extend from a surface 28 of port 16. Engagement elements 17 and 18 are circular in shape and spaced apart by a distance $d_3$.

Figure 15B:
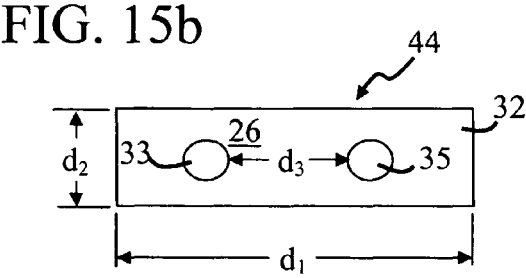
FIG. 15b is a view of a connector included in FIG. 6a taken along a cut line 15b-15b'.

FIG. 15b is a view of connector 44 taken along a cut line 15b-15b' of FIG. 6a. Housing 32 of connector 44 also has a rectangular shape with length dimension $d_1$ and width dimension $d_2$ so that it can be received by port 16. Complementary engagement elements 33 and 32 are spaced apart from each other by distance $d_3$ and have the same shape as engagement elements 17 and 18. In this way, when housing 32 is received by port 16, complementary engagement elements 33 and 35 are received by corresponding engagement elements 17 and 18 and electrical contact is made therebetween. In this example, housing 32 is received by port 16 when surface 28 abuts a surface 26 of housing 32.

Figure 15C:
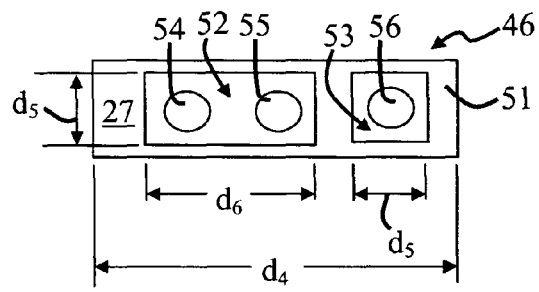
FIG. 15c is a view of another connector included in FIG. 6a taken along a cut line 15c-15c'.

FIG. 15c is a view of connector 46 taken along a cut line 15c-15c' of FIG. 6a. Port 52 has a rectangular shape with a length dimension of $d_6$ and a width dimension of $d_5$. Port 16 extends through a surface 27 of housing 51 and engagement elements 54 and 55 extend from port 52. Engagement elements 54 and 55 are circular in shape and spaced apart by a distance $d_8$. Port 53 is square in shape with length and width dimensions of $d_5$.

Figure 15D:
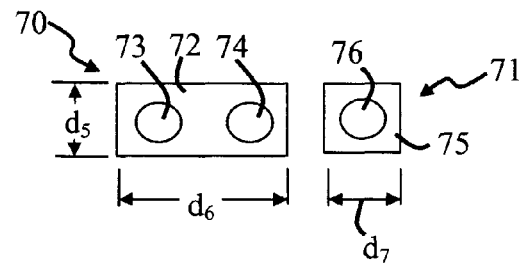
FIG. 15d is a view of another connector of FIG. 6a taken along a cut line 15d-15d'.

FIG. 15d is a view of connectors 70 and 71 taken along a cut line 15d-15d' of FIG. 6a. Housing 72 of connector 110 also has a rectangular shape with length dimension $d_6$ and width dimension $d_5$ so that it can be received by port 52. Complementary engagement elements 73 and 74 are spaced apart from each other by distance $d_8$ and have the same shape as engagement elements 54 and 55. In this way, when housing 72 is received by port 52, complementary engagement elements 73 and 74 are received by corresponding engagement elements 54 and 55 and electrical contact is made therebetween. In this example, housing 72 is received by port 52 when surface 28 is moved towards a surface 26 of housing 32.

Figure 16A:
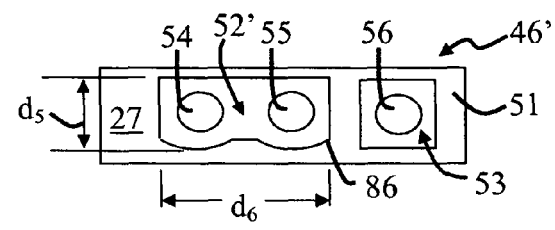

FIG. 16a is a view of another embodiment of connector 46 taken along cut line 15c-15c' of FIG. 6a. This embodiment is designated as connector 46' for ease of discussion. In this example, port 52' is similar to port 52, except that it has a different shape. In particular, port 52' includes a side 86 that is curved so that port 52' cannot receive connector 70 (FIG. 15d) as described above. In this way, connector 70 is incompatible with connector 46'.

Figure 16B:
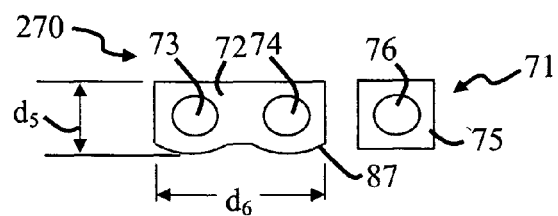

FIG. 16b is a view of a connector 270 that is compatible with connector 46'. Connector 270 is similar to connector 70 except it has a surface 87 that is the same shape as surface 86. In this way, connector 270 can be received by port 52' so that surfaces 86 and 87 abut each other. It is preferable that the various connectors described herein have a distinct color to aid in their use. For example, connectors 46 and 70 can both be red to indicate that they are both compatible with each other and connectors 46' and 270 can both be blue to indicate that they are compatible with each other.

It should be noted that patient side portion 43 can be used as a connector in some embodiments and an adapter in others. For example, patient side portion 43 is used as a connector in FIGS. 15a, 15b, 15c, and 15d because the connectors are compatible with each other. In another example, patient side portion 43 is used as an adapter when the various connectors are not compatible. For example, There are a few adapters in the art for use with AEDs. Examples include the DAC-300 Quik-Combo Pad Adapter made by Medtronic and the Defibtech DDP-100 adapter. However, the configuration of the electrode set coupled to them cannot be changed. For example, a third electrode cannot be added to the DAC-300 or DDP-100 adapters.

Figure 17A:
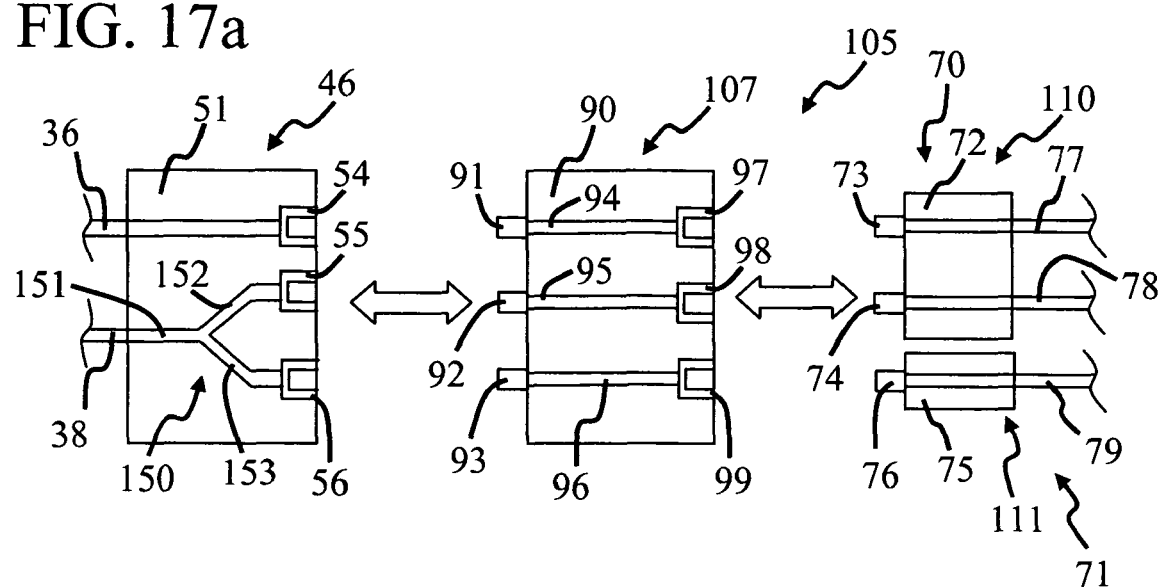
FIGS. 17a and 17b are diagrams of different embodiments of physiological stimulator connector systems, in accordance with the present invention.
Figure 17B:
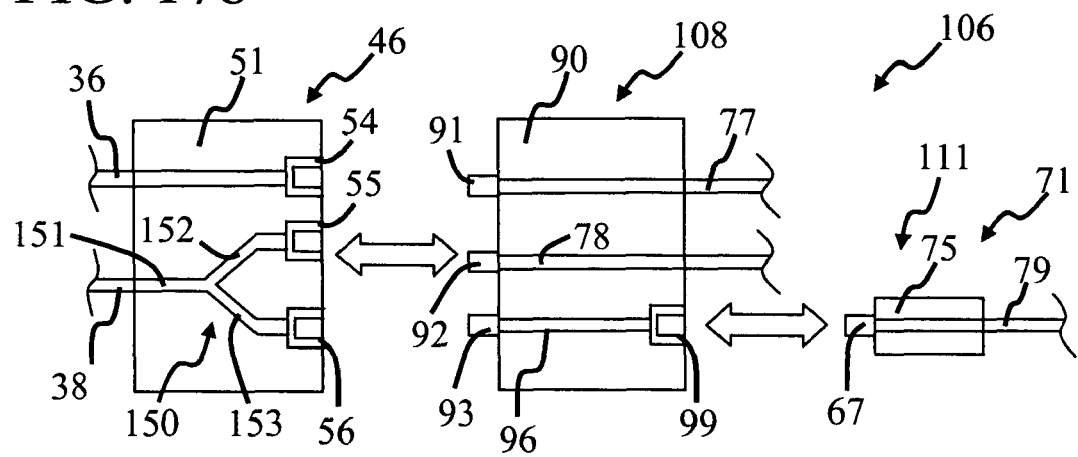

FIGS. 17a and 17b are diagrams of physiological stimulator connector systems 105 and 106, respectively, in accordance with the present invention. In FIG. 17a, connector system 105 includes physiological connector 46 as discussed with FIG. 6a and connectors 110 and 111 as discussed with FIGS. 5 and 6a. In this example, electrode sets 70 and 71 are in communication with connector 46 through a connector 107. In other examples, other electrode sets can be used, such as electrode sets 70' and 242, as described with FIG. 5.

Connector 107 includes a housing 90 which carries engagement elements 97, 98, and 99. Engagement elements 97, 98, and 99 are connected to complementary engagement elements 91, 92, and 93, respectively, through corresponding conductive lines 94, 95, and 96. Engagement elements 97 and 98 are shaped and dimensioned to receive engagement elements 73 and 74, respectively, and engagement element 99 is shaped and dimensioned to receive engagement element 76. Further, engagement elements 54, 44, and 56 are shaped and dimensioned to receive engagement elements 91, 92, and 93, respectively. In this way, connector 107 is repeatably moveable between engaged and disengaged positions with connector 46 and connectors 70 and 71 are repeatably moveable between engaged and disengaged positions with connector 107.

In operation, connectors 70 and 71 are engaged with connector 107 as described above. Connector 107 is then engaged with connector 46. In this way, connectors 70 and 71 are coupled to conductive lines 36 and 38 together instead of separately. If desired, connector 107 is disengaged from connector 46 so that connectors 70 and 71 are decoupled from conductive lines 36 and 38 together instead of separately. Connector 107 can then be engaged to another connector connected to another physiological stimulator. This is useful in instances when the patient is being transferred from the medical equipment of one responder to that of another responder. The various connections is faster because it requires fewer movements. A single movement is used to engage and disengage more than one electrode set to a physiological stimulator. In one example, the medical equipment of the BLS first responder is an AED and that of the second responder is an ALS defibrillator, which is typically carried by paramedics. The emergency equipment of a third responder is that of a hospital. This is useful when transferring the patient between the equipment used by the first responder and the second responder, such as a paramedic. In most instances, the patient is then transferred from the second responder to a third responder, such as hospital personnel.

In FIG. 17b, connector system 106 includes connector 46 and connector 71. Connector 71 is coupled to connector 106 through a connector 108. In this example, connector 108 includes engagement elements 91 and 92 coupled to conductive lines 77 and 78, respectively. Connector 108 also includes engagement element 99 coupled to complementary engagement element 93 through conductive line 96. Engagement element 99 is shaped and dimensioned to receive engagement element 76 of connector 71. In this way, connector 108 is repeatably moveable between engaged and disengaged positions with connector 46 and connector 71 is repeatably moveable between engaged and disengaged positions with connector 108.

In operation, connector 71 is engaged with connector 108 as described above. Connector 108 is then engaged with connector 46. In this way, connector 71 is coupled to conductive line 38 together with connector 108 instead of separately. If desired, connector 108 is disengaged from connector 46 so that connector 71 is decoupled from conductive line 38 together instead of separately. Connector 108 can then be engaged to another connector connected to another physiological stimulator.

This is useful in instances when a previous responder is using two electrode pads and the current responder wants to add a third electrode pad. The third electrode pad can be an anterior-sternum pad or it can be a posterior pad.

This is useful in instances when the patient is being transferred from the medical equipment of one responder to that of another responder. The various disconnections and connections are faster because they require fewer movements. A single movement is used to engage and disengage more than one electrode set to a physiological stimulator. In one example, the medical equipment of the BLS first responder is an AED and that of the second responder is an ALS defibrillator, which is typically carried by paramedics. The emergency equipment of a third responder is that of a hospital. This is useful when transferring the patient between the equipment used by the first responder and the second responder, such as a paramedic. In most instances, the patient is then transferred from the second responder to a third responder, such as hospital personnel.

The embodiments of the invention described herein are exemplary and numerous modifications, variations and rearrangements can be readily envisioned to achieve substantially equivalent results, all of which are intended to be embraced within the spirit and scope of the invention as defined in the appended claims.

The invention claimed is:

1. Apparatus, comprising:
a physiological power source having conductive lines for applying therapy to a patient, the physiological power source configured to generate and send signals through the conductive lines and configured to monitor and receive signals through the conductive lines, the signals being defined as a defibrillation signal, a pacing signal, and a monitoring signal;
first, second, and third electrode pads in communication with the conductive lines and adapted to be attached externally to the patient, each of the electrode pads configured to receive through the conductive lines defibrillation and pacing signal to the patient, and each of the electrode pads configured to send through the conductive lines to the physiological power source monitoring signals, such that each of the first, second, and third electrode pads are capable in different combinations thereof of alternating between delivering said defibrillation and pacing signals to the patient and between delivering monitoring signals to the physiological power source particularly when the first electrode is positioned on the patient in an anterior apex position, the second electrode is positioned on the patient in an anterior sternum position, and the third electrode is positioned on the patient in a posterior position; and the physiological power source further including modes of operation defined by at least a first mode and a second mode of operation and the physiological power source configured to switch between modes of operation while applying therapy to the patient, wherein the first mode of operation is defined by the physiological power source being configured to receive monitoring signals from the first electrode pad, being configured to send pacing signals to the third electrode pad, and further configured to alternate between receiving monitoring signals and sending pacing signals to the second electrode pad; and wherein the second mode of operation is defined by the physiological power source being configured to send defibrillation signals to the first, second and third electrode pads.

2. The apparatus of claim 1 further comprising
a connector having a signal coupler/decoupler, and being secured to the conductive lines, the coupler/decoupler capable of combining signals flowing to the physiological power source and for separating a signal flowing away from the physiological power source.

3. The apparatus of claim 2, further including a physiological cable which carries the signal coupler/decoupler, the physiological cable being in communication with the physiological power source.

4. The apparatus of claim 2, wherein the signal coupler/decoupler has an adjustable impedance.

5. The apparatus of claim 2, wherein only the second and third electrode pads are coupled to the signal coupler/decoupler.

6. The apparatus of claim 5, wherein the signal coupler/decoupler has an impedance to adjust the impedance between the second and third electrode pads.

* * * * *